United States Patent
Welch et al.

[11] Patent Number: 6,117,285
[45] Date of Patent: Sep. 12, 2000

[54] SYSTEM FOR CARRYING OUT STERILIZATION OF EQUIPMENT

[75] Inventors: William D. Welch, Agoura Hills, Calif.; Daniel L. Robinson, Salt Lake City, Utah

[73] Assignee: Medical Discoveries, Inc., Salt Lake City, Utah

[21] Appl. No.: 08/838,252

[22] Filed: Apr. 17, 1997

Related U.S. Application Data

[63] Continuation-in-part of application No. 08/633,231, Apr. 16, 1996, Pat. No. 6,007,686, which is a continuation-in-part of application No. 08/296,970, Aug. 26, 1994, Pat. No. 5,507,932.

[51] Int. Cl.[7] .............................. C25B 15/00; C25B 9/00
[52] U.S. Cl. ...................... 204/237; 204/271; 204/272; 204/275
[58] Field of Search ................................... 204/271, 272, 204/275, 237; 205/701

[56] References Cited

U.S. PATENT DOCUMENTS

| | | |
|---|---|---|
| 998,982 | 7/1911 | Pier . |
| 1,159,699 | 11/1915 | Murdock et al. . |
| 3,076,754 | 2/1963 | Evans . |
| 3,282,823 | 11/1966 | Richards . |
| 3,443,055 | 5/1969 | Gwynn et al. . |
| 3,479,275 | 11/1969 | Gwynn et al. . |

(List continued on next page.)

FOREIGN PATENT DOCUMENTS

| | | |
|---|---|---|
| 55-87712 | 7/1980 | Japan . |
| 56-32422 | 4/1981 | Japan . |
| 5 632 422 | 4/1981 | Japan . |
| 1- 259001 | 10/1989 | Japan . |
| 3-38293 | 2/1991 | Japan . |
| 3-270784 | 12/1991 | Japan . |
| 6-31276 | 2/1994 | Japan . |
| 6-31277 | 2/1994 | Japan . |
| 6-31278 | 2/1994 | Japan . |
| 6-55173 | 3/1994 | Japan . |
| 6-55174 | 3/1994 | Japan . |
| 6-55175 | 3/1994 | Japan . |
| 6-71265 | 3/1994 | Japan . |
| 6-71266 | 3/1994 | Japan . |
| 6-71267 | 3/1994 | Japan . |
| 6-114375 | 4/1994 | Japan . |
| 6-114376 | 4/1994 | Japan . |
| 6-114377 | 4/1994 | Japan . |
| 6-165982 | 6/1994 | Japan . |
| 6-165983 | 6/1994 | Japan . |
| 6-165984 | 6/1994 | Japan . |
| 6-165985 | 6/1994 | Japan . |

(List continued on next page.)

OTHER PUBLICATIONS

Adams, V.D., et al., "Electrolytic Degradation of Toxic Organics: Analyses of Ozone and Chlorine," *Tennessee Technological University Report* No Date.

(List continued on next page.)

*Primary Examiner*—Donald R. Valentine
*Attorney, Agent, or Firm*—Thorpe, North & Western, LLP

[57] ABSTRACT

An apparatus for electrolyzing fluids. The resulting electrolyzed fluids are particularly suited for treating physiological materials such as whole blood, plasma, or cell isolates in order to reduce the effect of harmful microorganisms. A container holds the fluid and a power supply provides a source of electrical current to an anode and a cathode positioned within the container. The system is particularly suited for disinfecting and/or sterilizing health care instruments. The instruments are bathed in the electrolyzed saline solution. If the instrument includes internal conduits the system of the present invention also preferably flows the electrolyzed saline solution through such conduits also to provide both cleaning and sterilization. The electrolyzed saline solution is recirculated from the electrodes to the instrument being sterilized. Embodiments of the invention are particularly suited to sterilizing dental drill handpieces without damage to the handpieces.

30 Claims, 14 Drawing Sheets

U.S. PATENT DOCUMENTS

| | | |
|---|---|---|
| 3,616,355 | 10/1971 | Themy et al. . |
| 3,718,540 | 2/1973 | Bailey . |
| 3,779,707 | 12/1973 | Tabone . |
| 3,819,329 | 6/1974 | Kaestner et al. ............... 204/271 X |
| 3,921,630 | 11/1975 | McPhee . |
| 3,996,126 | 12/1976 | Rasmussen ........................ 204/271 |
| 4,010,085 | 3/1977 | Carlin . |
| 4,054,998 | 10/1977 | Hesselgren . |
| 4,201,651 | 5/1980 | Themy . |
| 4,236,992 | 12/1980 | Themy . |
| 4,316,787 | 2/1982 | Themy . |
| 4,327,060 | 4/1982 | Nisii . |
| 4,362,241 | 12/1982 | Williams . |
| 4,382,788 | 5/1983 | Pelerin . |
| 4,400,357 | 8/1983 | Hohmann . |
| 4,448,750 | 5/1984 | Fuesting . |
| 4,541,992 | 9/1985 | Jerge et al. . |
| 4,545,956 | 10/1985 | Ciszewski et al. . |
| 4,552,163 | 11/1985 | Biancalana et al. . |
| 4,560,455 | 12/1985 | Porta et al. .................. 204/271 X |
| 4,710,233 | 12/1987 | Hohmann et al. . |
| 4,752,444 | 6/1988 | Bowen et al. . |
| 4,761,208 | 8/1988 | Gram et al. . |
| 4,839,004 | 6/1989 | Castellini ..................... 205/701 X |
| 4,938,854 | 7/1990 | Sharifian et al. . |
| 4,968,616 | 11/1990 | Inoue et al. . |
| 4,970,216 | 11/1990 | Deckner et al. . |
| 4,976,959 | 12/1990 | Berger et al. . |
| 5,028,588 | 7/1991 | Hoffman et al. . |
| 5,250,160 | 10/1993 | Oksman et al. ................. 205/701 |
| 5,316,740 | 5/1994 | Baker et al. . |
| 5,334,383 | 8/1994 | Morrow . |
| 5,385,711 | 1/1995 | Baker et al. . |
| 5,462,644 | 10/1995 | Woodson . |
| 5,507,932 | 4/1996 | Robinson . |
| 5,560,816 | 10/1996 | Robinson . |
| 5,622,848 | 4/1997 | Morrow . |

FOREIGN PATENT DOCUMENTS

| | | |
|---|---|---|
| 6-165986 | 6/1994 | Japan . |
| 6-165987 | 6/1994 | Japan . |
| 6-178979 | 6/1994 | Japan . |
| 6-178980 | 6/1994 | Japan . |
| 6-178981 | 6/1994 | Japan . |
| 6-226259 | 8/1994 | Japan . |
| 6-226260 | 8/1994 | Japan . |
| 6-246263 | 9/1994 | Japan . |
| 6-246264 | 9/1994 | Japan . |
| 6-246265 | 9/1994 | Japan . |
| 6-246266 | 9/1994 | Japan . |
| 6-246267 | 9/1994 | Japan . |
| 6-246268 | 9/1994 | Japan . |
| 6-246269 | 9/1994 | Japan . |
| 6-246270 | 9/1994 | Japan . |
| 6-246271 | 9/1994 | Japan . |
| 6-254564 | 9/1994 | Japan . |
| 6-254565 | 9/1994 | Japan . |
| 6-254566 | 9/1994 | Japan . |
| 6-292892 | 10/1994 | Japan . |
| 6-304565 | 11/1994 | Japan . |
| 6-312184 | 11/1994 | Japan . |
| 6-312185 | 11/1994 | Japan . |
| 6-328079 | 11/1994 | Japan . |
| 6-328071 | 11/1994 | Japan . |
| 6-312186 | 11/1994 | Japan . |
| 6-3354684 | 12/1994 | Japan . |
| 7-042463 | 1/1995 | Japan . |
| 7-068265 | 3/1995 | Japan . |
| 7-136659 | 5/1995 | Japan . |
| 7-136660 | 5/1995 | Japan . |
| 7-148490 | 6/1995 | Japan . |
| 7-185552 | 7/1995 | Japan . |
| 7-185553 | 7/1995 | Japan . |
| 7-190989 | 7/1995 | Japan . |
| 7-195076 | 8/1995 | Japan . |
| 7-204648 | 8/1995 | Japan . |
| 7-204650 | 8/1995 | Japan . |
| 7-204651 | 8/1995 | Japan . |
| 7-204652 | 8/1995 | Japan . |
| 7-204653 | 8/1995 | Japan . |
| 7-214060 | 8/1995 | Japan . |
| 7-214076 | 8/1995 | Japan . |
| 7-222977 | 8/1995 | Japan . |
| 7-236888 | 9/1995 | Japan . |
| 7-258099 | 10/1995 | Japan . |
| 7-284775 | 10/1995 | Japan . |
| 7-290054 | 11/1995 | Japan . |
| 7-290064 | 11/1995 | Japan . |
| 7-290065 | 11/1995 | Japan . |
| 7-323287 | 12/1995 | Japan . |
| 7-328639 | 12/1995 | Japan . |
| 7-328640 | 12/1995 | Japan . |
| 8-010766 | 1/1996 | Japan . |
| 8-010767 | 1/1996 | Japan . |
| 8-010771 | 1/1996 | Japan . |
| 8-015218 | 1/1996 | Japan . |
| 8-019782 | 1/1996 | Japan . |
| 8-071563 | 3/1996 | Japan . |
| 8-103770 | 4/1996 | Japan . |
| 8-108181 | 4/1996 | Japan . |
| 8-126885 | 5/1996 | Japan . |
| 8-141569 | 6/1996 | Japan . |
| 8-168762 | 7/1996 | Japan . |
| 8-168768 | 7/1996 | Japan . |
| 8-182987 | 7/1996 | Japan . |
| 8-192158 | 7/1996 | Japan . |
| 8-299956 | 11/1996 | Japan . |
| 8-308909 | 11/1996 | Japan . |
| 8-323366 | 12/1996 | Japan . |
| 9-010772 | 1/1997 | Japan . |
| 0 820 275 | 9/1959 | United Kingdom . |
| WO 96 02271 | 2/1996 | WIPO . |
| WO 96 06959 | 3/1996 | WIPO . |

OTHER PUBLICATIONS

Finch, G.R., et al., "Comparatice Inactivation of Poliovirus Type 3 and Coliphage in Demand–Free Phosphate Bufferby Using Ozone," *Applied and Environmental Microbiolgy*, vol. 57, No. 11, pp. 3121–6 (1991). No date.

Hayashi, H., et al., "Successful Treatment of Mediastinitis after Cardiovascular Surgery Using Electrolyzed Strong Acid Aqueous Solution," *Artificial Organs*, vol. 21, No. 1, pp. 39–42 (1997). No Month.

Morrow, R., et al., "Inhibition of HIV Activity in vitro and in vivo by MDI–P," Abstract #PA0321 No Date.

Morrow, R.E., et al., "Inhibition of HIV Activity by a Noncytotoxic Solution of Ozone, HOCl, OCl and Cl (Feb. 7, 1994),"Poster Board Abstract for HIV Clinical Trials Conference, Alexandria, VA, Mar. 24, 1994.

Sato, H., et al., "Virucidal Effect of Ozone Treatment of Laboratory Animal Viruses," *Experimental Animals*, vol. 39, No. 2, pp. 223–229 (1990). No Month.

Wagner, S.J., et al., "Approaches to the Reduction of Viral Infectivity in Cellular Blood Components and Single Donor Plasma," *Transfusion Medicine Reviews*, vol. 5, No. 1, pp. 18–32 (1991). No Month.-

Wells, K.H., et al., "Inactivation of Human Immunodeficiency Virus Type 1 by Ozone in vitro," *Blood,* vol. 78, No. 7, pp. 1882–1890 (1991). No Month.

Wilk, I.J., et al., "Antimicrobial Activity of Electrolyzed Saline Solutions," *The Science of the Total Environment,* vol. 63, pp. 191–197 (1987). No Month.

Wilson, A., "FDA Assails Machine in Court," *Salt Lake Tribune,* Salt Lake City, UT, pp. D1, Thursday, Mar. 31, 1994.

"Simple, Safe and Economical Way to Disinfect Municipal Drinking Water," Brinecell Inc., Salt Lake City, UT, Mar. 1992.

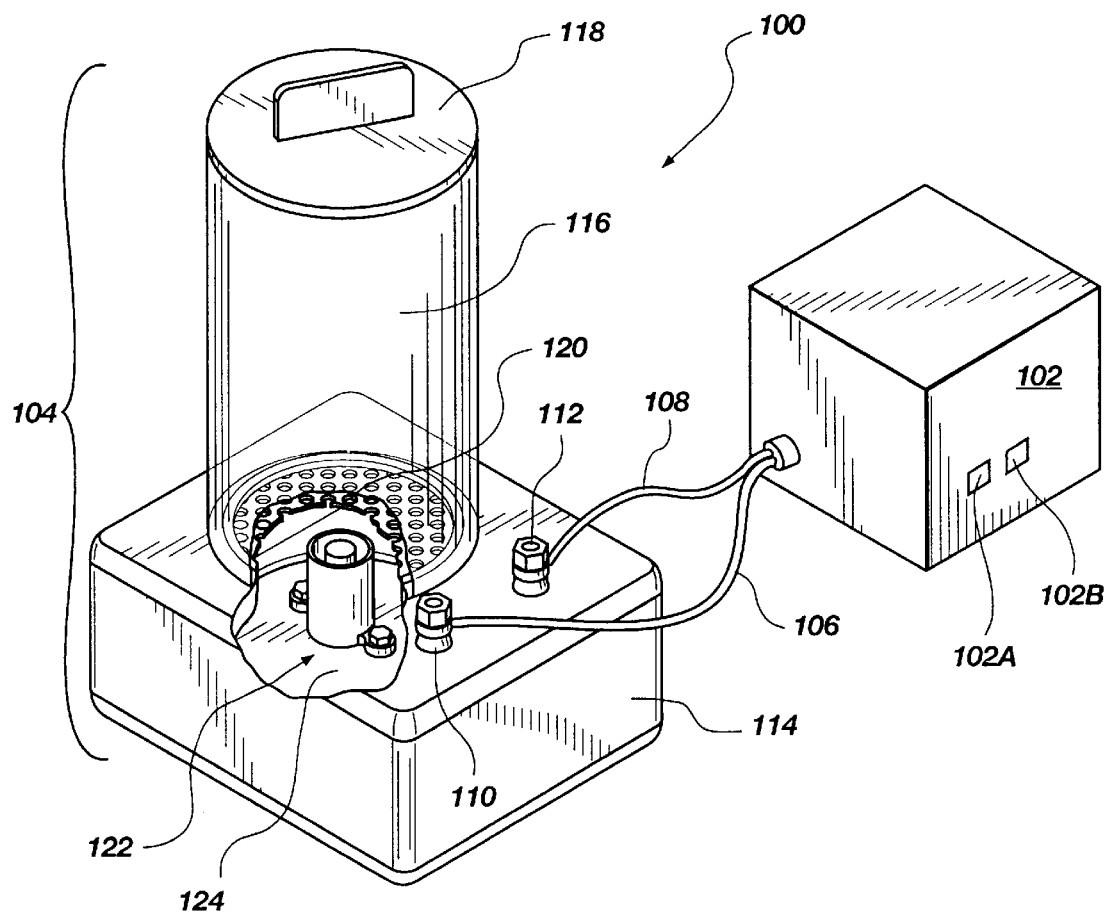
Fig. 1
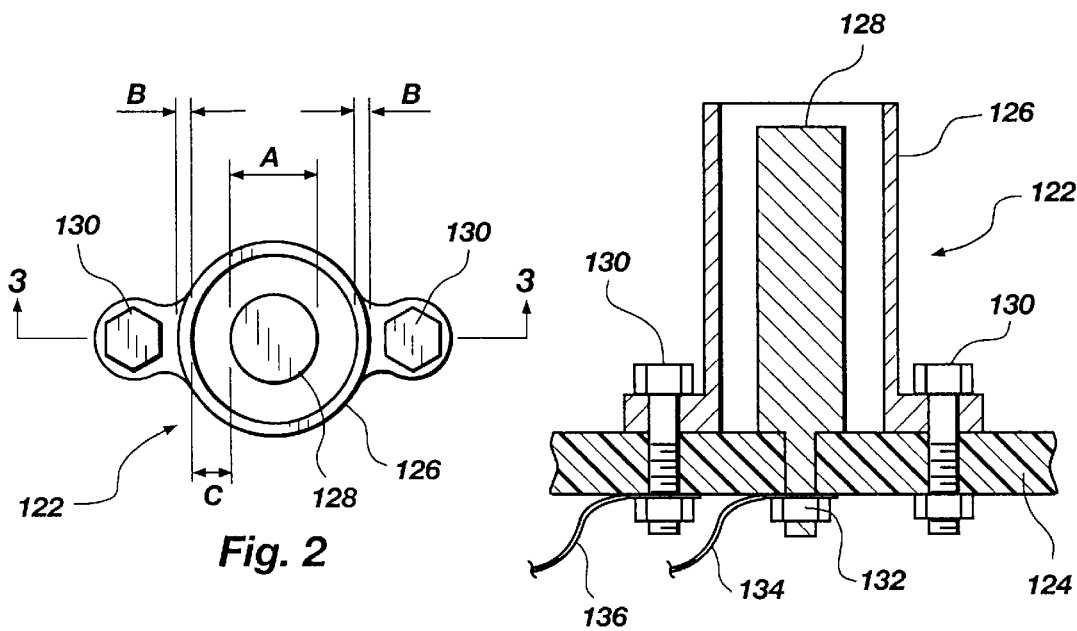
Fig. 2   Fig. 3

SYSTEM FOR CARRYING OUT STERILIZATION OF EQUIPMENT

BACKGROUND

1. Related Applications

This application is a continuation-in-part of prior U.S. patent application Ser. No. 08/633,231 filed Apr. 16, 1996, now U.S. Pat. No. 6,007,686 which is a continuation-in-part of prior U.S. Ser. No. 08/296,970 filed Aug. 26, 1994, now U.S. Pat. No. 5,507,932.

2. The Field of the Invention

This invention relates to apparatus and methods for electrolyzing fluids and more particularly relates to apparatus and methods for electrolyzing saline solutions for use as antimicrobial agents.

3. The Prior Art

It has long been known that the electrolysis of fluids can result in useful products. In particular, the electrolysis of saline solution results in the production of chlorine and ozone. It is known that the products resulting from the electrolysis of saline solutions are useful as in vitro microbicides for hard surfaces. Thus, various apparatus and methods have been proposed for electrolyzing saline solution, however, all of the previously available schemes present one or more drawbacks. For example, while the electrolyzed saline solution is useful in some cases as an in vitro microbicide, past uses have posed problems and may not destroy harmful pathogens. Moreover, the drawbacks of previously proposed schemes for electrolyzed saline solution are particularly disadvantageous when the electrolyzed saline solutions are to be used for in vivo administration.

For example, U.S. Pat. Nos. 4,236,992, 4,238,323, and 4,316,787 all to Themy disclose an electrode, method and apparatus for electrolyzing dilute saline solutions to produce effective amounts of disinfecting agents such as chlorine, ozone and hydroxide ions. Significantly, the devices disclosed in Themy all are inefficient, produce unpredictable results, and potentially introduce undesirable and toxic substances into the electrolyzed solution. The unpredictable results obtained using the devices disclosed in Themy makes the resulting product unsuitable for use as an antimicrobial agent. Moreover, the introduction of undesirable and toxic substances into the electrolyzed solution is of critical concern when the solution is to be administered in vivo to a patient.

Another apparatus for producing electrolyzed saline solutions has been available under the trade name Ster-O-Lizer. Laboratory reports and other data available from testing of electrolyzed saline solutions from various Ster-O-Lizer models have shown that it is effective in keeping water free of pathogenic organisms. Tests conducted in vitro further show that certain microorganisms, inclusive of *Pseudomonas aeruginosa, Escherichia coli, Staphylococcus aureus, Candida albicans,* and *Salmonella typhi,* are non-infectious after exposure to electrolyzed saline solutions. Nevertheless, devices such as those available under the trade name Ster-O-Lizer do not address the particular problems which are posed when medical or dental equipment is to be sterilized. Such devices also do not address the critical concerns which arise when the resulting solution is to be administered in vivo to a patient.

For many years, ozone ($O_3$) has been used for the treatment of viral infections. Chlorine, in the form of chlorinated lime, was used successfully as early as 1846 to prevent and fight puerperal fever. By 1911, the United States purified as much as 800,000,000 gallons of water through the chlorination process. Wide use of chlorine as a 0.05% sodium hypochlorite solution (Dakins Solution) for treatment of open and infected wounds began in 1915. Dakins Solution was a standard product up to 1963 which was listed in the British Pharmacopeia.

As reported by Wilk et al., *International Congress on Technology and Technology Exchange,* First Euro-American Symposium, Paris, France (1992) and *Science, Total Environment,* 63:191–197 (1987), certain combinations of ozone and chlorine have significantly greater activity than either used separately against a variety of bacteria including *Staphylococcus aureus* and *Pseudomonas aeruginosa. Candida albicans* was also reported to be effectively killed by a combination of ozone and chlorine.

In view of the many uses of chlorine and ozone, numerous apparatus and methods have been proposed for generating chlorine and ozone. Significantly, the previously available apparatus and methods have not been well-suited to producing electrolyzed saline containing correct amounts of ozone and chlorine for in vitro destruction of microbes on health care equipment or in vivo treatment of physiological fluids for the destruction of microbes in warm blooded animals, including humans. It has recently been discovered that there are situations where physiological fluids can be beneficially treated using electrolyzed saline solutions. The treatment of physiological fluids such as whole blood, plasma or cell isolates by electrolyzed saline solution, said treatment rendering these fluids benign from infectious organisms without destroying the therapeutic characteristics of such fluids, is now possible. Disadvantageously, the available apparatus and methods for generating chlorine and ozone are not well-suited for either in vitro destruction of microorganisms or for either in vitro or in vivo treatment of physiological fluids such as whole blood, plasma, or cell isolates.

Methods for treatment of physiological fluids using electrolyzed solutions are set forth in U.S. Pat. No. 5,334,383 and U.S. patent application Ser. No. 08/275,904 filed Jul. 15, 1994, both of which are now incorporated herein by reference in their entireties. In these documents, an electrolyzed saline solution, properly made and administered in vivo, is effective in the treatment of various infections brought on by invading antigens and particularly viral infections. Thus, it would be a great advance in the art to provide an apparatus and method for electrolyzing saline solution for administration in vivo.

There is also great concern in the health care profession with the transfer of infectious organisms from one patient to another. In many cases, the concern over cross contamination between patients has lead to the development and use of health care equipment which, rather than being sterilized and reused, is disposed of after a single use eliminating any possibility of cross contamination of infectious organisms between patients due to reuse of that equipment. In many instances of health care equipment, it is impossible or impractical to dispose of all components after contact with a single patient. While a properly maintained and operated autoclave will kill all pathogens, many items of health care equipment are damaged or destroyed by the high temperatures used in an autoclave. Also, there are many other items which would benefit from sterilization but which cannot withstand the treatment provided by an autoclave. Thus, it would also be an advance in the art to provide a system and method for disinfecting and/or sterilizing health care equipment to prevent the transfer of harmful pathogens from one patient to another patient.

BRIEF SUMMARY AND OBJECTS OF THE INVENTION

In view of the above described state of the art, the present invention seeks to realize the following objects and advantages.

It is one primary object of the present invention to prevent the transfer of harmful microbes via health care equipment from one patient to another patient.

It is another object of the present invention to provide a system and method for sterilizing health care instruments.

It is a further object of the present invention to provide a system and method for sterilizing medical and dental instruments which is effective and not damaging to the instruments.

It is still another object of the present invention to provide a system and method for inactivating infectious spores present on medical and dental instruments to prevent infection of a subsequent patient without damaging the instrument.

It is also an object of the present invention to provide an apparatus and method for electrolyzing saline solutions which are particularly suitable for administration in vivo.

It is a further object of the present invention to provide system and method for decreasing the viability of microbes on processed and fresh foods.

It is also an object of the present invention to provide an apparatus and method for electrolyzing fluids which does not introduce harmful substances into the fluid.

It is a further object of the present invention to provide an apparatus and method for electrolyzing saline solutions which is reliable and can be economically operated.

These and other objects and advantages of the invention will become more fully apparent from the description and claims which follow, or may be learned by the practice of the invention.

The present invention provides an apparatus for electrolyzing fluids. Some embodiments of the invention are particularly suited for producing electrolyzed fluids, such as a saline solution, which are particularly suited for treating physiological materials such as whole blood, plasma or cell isolates, or other biological materials, in order to reduce the effect of harmful microorganisms and are well suited for in vivo administration to a warm blooded animals, including humans. Other embodiments of the invention are particularly suited for producing electrolyzed fluids for disinfecting and sterilizing medical and dental instruments, as well as other items, and for applying such a solution to such instruments and items.

A preferred embodiment of the present invention includes a container means for holding a fluid which is to be electrolyzed. A power supply means provides a source of electrical current. At least a first anode and a second anode are connected to the power supply means. The anodes and cathodes are positioned within the container means so as to be immersed in the fluid to be electrolyzed.

The anode preferably comprises a base metal. The base metal is a metal selected from the group consisting of titanium, niobium, platinum, and tantalum, preferably niobium. Preferably, an outer layer of platinum is bonded to the base. The anode comprises a cylindrical shape.

The cathode is also connected to the power supply means and comprises a metal and also has a substantially cylindrical shape. The cathode is positioned concentrically in relation to the anode. The spacing between the cathode and the anode is not greater than a preferred amount. Moreover the voltage potential between the cathode and the anode is not greater than a preferred amount. The combination of the close electrode spacing, the low voltage used, and the materials used to fabricate the electrodes, result in a fluid with about 5 to about 100 mg/L of ozone and a free chlorine content in the range from about 5 to about 300 ppm and a pH in the range from about 7.2 to about 7.6.

Some embodiments of the present invention provide a system for disinfecting and/or sterilizing health care equipment, such as medical and dental instruments. The preferred embodiments of the invention used for sterilization includes a means for electrolyzing a saline solution to produce an electrolyzed saline solution. The instruments are held in a means for holding the instrument, for example a tray, and are bathed in the electrolyzed saline solution. If the instrument includes internal conduits the system of the present invention also preferably flows the electrolyzed saline solution through such conduits also to provide both cleaning and sterilization. The electrolyzed saline solution is preferably recirculated from the means for electrolyzing to the instrument being sterilized.

Some preferred embodiments of the present invention are particularly suited to sterilizing dental drill handpieces. While dental drill handpieces are routinely damaged by the high temperatures experienced using an autoclave, the embodiments of the present invention carry out sterilization of dental drill handpieces substantially without damage to the handpieces. The present invention provides effective sterilization of medical and dental instruments which is more efficient and more easily carried out than other available methods of serialization and, particularly in the case of dental drill handpieces, avoids damage to the instrument which can occur when high temperatures are used to provide sterilization. In accordance with one particular aspect of the present invention, a surfactant is added to the sterilizing fluid and the rotation of the dental drill handpiece is controlled to greatly improve the efficiency of the sterilization process.

BRIEF DESCRIPTION OF THE DRAWINGS

In order to better appreciate how the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which:

FIG. 1 is a perspective view of a first presently preferred embodiment of the present invention.

FIG. 2 is a detailed top view of the electrode assembly represented in FIG. 1.

FIG. 3 is a side cross sectional view of the electrode assembly taken along line 3—3 in FIG. 2.

DETAILED DESCRIPTION OF THE PREFERRED EMBODIMENTS

Figure 3A:
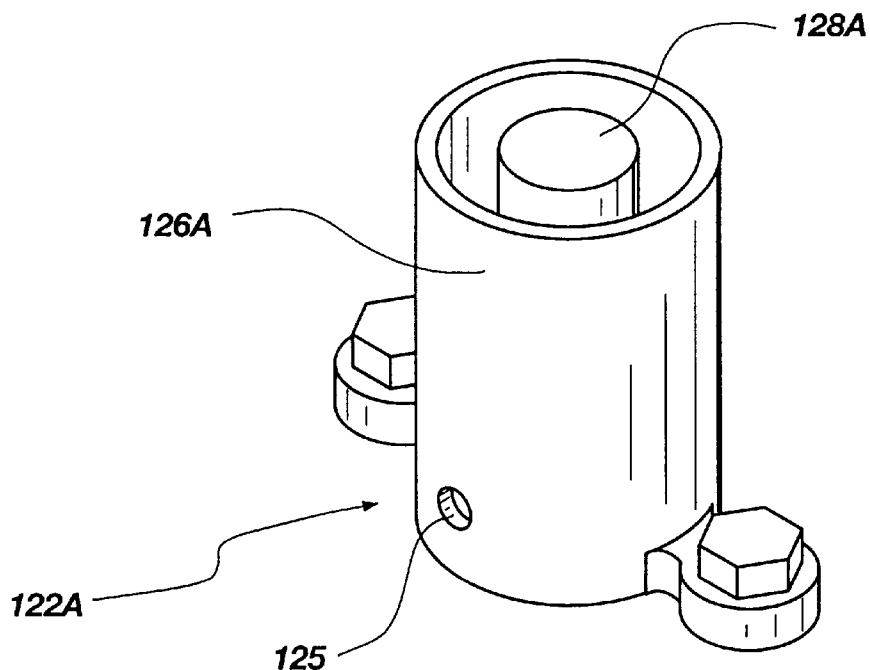
FIG. 3A is a perspective view of another embodiment of the present invention which includes an alternate electrode structure.

Reference will now be made to the drawings wherein like structures will be provided with like reference designations.

Referring first to FIG. 1, which is a perspective view of a first presently preferred embodiment of the present invention generally represented at 100, includes a power supply 102 and a fluid receptacle represented at 104. The fluid receptacle 104 includes a base 114 upon which is attached a fluid vessel 116. The base 114 can preferably be fabricated from an insulative plastic material. The fluid vessel 116 is preferably fabricated from an inert and clear plastic material which is compatible with biological processes as available in the art. Importantly, it is preferred that the fluid vessel be a material which will not introduce undesirable substances into the fluid being electrolyzed. One preferred material for the fluid vessel is a polycarbonate material available in the industry. Also, it is preferred that the fluid vessel 116 be fabricated from a transparent material so that the electrolyzation of the fluid can be observed in progress and the process adjusted or interrupted if abnormalities are observed.

A lid 118 is provided to cover the fluid vessel 116 and keep contaminants out of the fluid vessel 116. A screen 120 is positioned to prevent foreign objects, which might accidentally fall into the fluid vessel 116, from falling to the bottom of the fluid vessel 116. The saline solution which is to be treated is placed into the fluid vessel 116, and the lid 118 is placed, for the necessary period of time after which the electrolyzed saline solution can be withdrawn from the fluid vessel 116, for example into a syringe, for use. The fluid vessel 116 is sealed at its bottom by a floor 124 which is attached to the interior of the base 114.

An electrode assembly, generally represented at 122, is attached to the floor 124 so that any fluid in the fluid vessel is exposed to the electrode assembly 122. The electrode assembly 122 is electrically connected to the power supply 102 via terminals 110 and 112 and cables 106 and 108, respectively. The power supply 102 should deliver a controlled voltage and current to the electrode assembly 122 when fluid is placed into the fluid vessel 116. The voltage and current applied to the electrode assembly 122 will vary according to the fluid being electrolyzed. To this end the power supply 102 includes means for adjustably limiting the voltage to a value not greater than about a maximum voltage. A device for setting and measuring the voltage 102A and a device for setting and measuring the current 102B is provided in the power supply 102. In accordance with the present invention, a low voltage of less than about 40 volts DC, or more preferably less than about 30 volts DC, is used. Exemplary voltage and current values, and the advantages which accrue when using the preferred voltage and current values, will be explained shortly.

FIG. 2 is a top view of the electrode assembly 122 represented in FIG. 1. The electrode assembly 122 preferably comprises a cylindrical inner electrode 128 and a cylindrical outer electrode 126. The inner electrode 128 is preferably solid. Alternatively, it is preferred that any hollow in the inner electrode is sealed so that fluid does not enter any such hollow. The cylindrical shape of the inner electrode 128 and the outer electrode 126 is preferred and results in better performance than obtained with electrodes of other shapes, e.g., elongated flat panels.

The diameter A of the inner electrode 128 is preferably about one-half inch. Other diameters A of the inner electrode can be selected by those skilled in the art in accordance with the information contained herein. The outer electrode 126 should be of a generally cylindrical shape and preferably be fabricated from any suitable metal. Metals such as titanium, niobium, platinum, and tantalum can preferably be used if their benefits are desired. The outer electrode 126 has a thickness (indicated at B in FIG. 2) which ensures that the inner electrode is shielded from potential physical damage. As will be appreciated, the indicated metals provide the advantage of resistance against corrosion which further prevents the introduction of harmful substances into the fluid being electrolyzed but other metals can be used within the scope of the present invention.

Still referring to FIG. 2, the space, indicated at C, between the inner electrode 128 and the outer electrode 126 does not exceed a maximum value. In contrast to previously available devices which separate the electrodes by greater distances and then utilize higher voltages to obtain the desired electrolyzation, the present invention preferably keeps the electrode spacing small and obtains improved performance over other schemes. It is preferred that the space between the inner electrode 128 and the outer electrode 126 be not more than about one-half (½) inch; it is more preferred that the space between the inner electrode 128 and the outer electrode 126 be not more than about three-eights (⅜) inch; and, it is most preferred that the space between the inner electrode 128 and the outer electrode 126 be not more than about one-quarter (¼) inch.

Reference will next be made to FIG. 3 which is a side cross sectional view of the electrode assembly taken along line 3—3 in FIG. 2. As seen in FIG. 3, the outer electrode 126 extends above the inner electrode 128 to provide improved electrical performance and physical protection. The outer electrode 126 is attached to the floor 124 by way of bolts 130, which extend through bores provided in the floor 124, and accompanying nuts. An electrical connection is made to the outer electrode 126 by a lead 136 attached to the bolt and nut. The lead 136 is attached to one of the terminals 110 or 112 (FIG. 1). Similarly, an electrical connection is made to the inner electrode 128 by a lead 134 which is held in place by a nut attached to a threaded stud extending from the bottom of the inner electrode and through a bore provided in the floor 124. The lead 134 is attached to the remaining one of the terminals 110 or 112 (FIG. 1). The leads 134 and 136 are kept insulated from any fluid which is present in the fluid vessel 116.

It is preferred that the inner electrode 128 function as the anode while the outer electrode function as the cathode when electrolyzing fluids and the power supply 102 and the terminals 110 and 112 should be properly arranged to carry this out.

It is recognized in the art that the anode is subject to destructive forces during electrolysis. In the devices found in the prior art, the anode of an electrode assembly may dissolve to the point of being inoperative and may need to be replaced very often. Critically, as the anode of an electrode assembly dissolves, the metallic components of the anode are dispersed into the fluid. If the fluid is a saline solution which will be used to treat physiological fluids, toxic substances dispersed into the solution, such as the materials comprising the anode, may be harmful or dangerous to the person who expects to be benefitted from the treatment.

Of all the possible materials for fabrication of the anode, the art recognizes that platinum is generally the least likely to be dissolved when used as an anode. Unfortunately, the cost of platinum often precludes the use of an anode which consists entirely of platinum. Thus, it is common in the art to utilize another metal as a base for the anode with a layer of platinum, or other resistant material, being placed on surfaces which contact the fluid to be electrolyzed.

One embodiment of the present invention advantageously utilizes an inner electrode 128, i.e., an anode, which includes a base of titanium or tantalum, and even more preferably niobium (also known as columbium), upon which a layer of platinum is provided wherever fluid contacts the anode. Significantly, niobium is a relatively good electrical conductor having a conductivity which is about three times greater than the conductivity of titanium. Moreover, if the base metal is exposed to the fluid, such as if a pinhole defect develops, toxic products are not produced by the contact between niobium and the fluid. Moreover, the high breakdown voltage in saline solution of the oxide which forms when a niobium base receives a layer of platinum provides further advantages of the present invention. It will be appreciated that the electrodes can be fabricated from many materials known in the art provided that the electrodes possess the necessary characteristics.

In one preferred apparatus, upon a base of niobium, a layer of platinum is formed on the anode. The layer of platinum is preferably formed using a technique referred to in the art as brush electrodeposition which can be carried out by those skilled in the art using the information set forth herein. Other techniques can also be used to form the platinum layer, such as tank (immersion) electrodeposition, vapor deposition, and roll bonding, but brush electrodeposition is preferred because of its superior adhesion and resulting less porosity than other economically comparable techniques.

The thickness of the platinum layer is preferably greater than about 0.02 mils and is most preferably greater than about 0.06 mils, and up to about 0.20 mils. The described combination of using niobium as a base for the anode of the electrode assembly and utilizing brush electrodeposition provides that the platinum layer can be much thinner than otherwise possible and still provide economical and reliable operation. It will be appreciated by those skilled in the art, that even with an anode fabricated in accordance with the present invention it may be necessary to replace the anode, which preferably comprises the inner electrode 128 represented in FIG. 3, after a period of use. The construction of the embodiments of the present invention facilitate replacement of the inner electrode 128 and the outer electrode 126 when it becomes necessary.

Figure 3B:
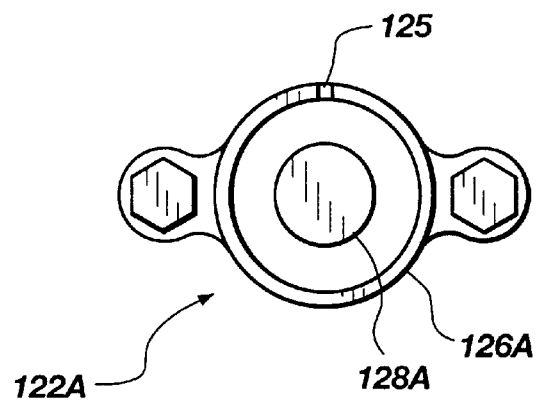
FIG. 3B is a detailed view of the alternate electrode structure represented in FIG. 3B.

Represented in FIG. 3A is another embodiment of the present invention which is the same as that represented in FIG. 1 except an alternative electrode assembly 122A has been implemented. The alternative electrode assembly 122A preferably is patterned after the electrode assembly 122 represented in FIGS. 1–3 with the inclusion of a fluid passageway 125 in the outer electrode 126A. As seen in the top view of FIG. 3B, the outer electrode 126A is provided with a fluid passageway 125 near its base while inner electrode 128A is preferably identical to inner electrode 128 represented in FIGS. 1–3.

The fluid passageway 125 provides fluid flow from the space between inner electrode 128A and outer electrode 126A. During operation, the fluid surrounding the electrode assembly 122A flows through the fluid passageway 125. The fluid flow through the fluid passageway 125 can occur as a result of currents which are induced in the fluid. It is also within the scope of the present invention to provide a device for causing the fluid to travel through the fluid passageway 125, for example, a pump structure can be used.

The fluid passageway 125, or some other structure performing the same functions, improves the efficiency and operation of the device. During operation of the electrode assembly 122A the inner electrode 128A, functioning as an anode, consumes chloride ions faster than the chloride ions can be replenished at the surface of the inner electrode 128A. The depletion of chloride ions at the surface of the inner electrode 128A causes a condition referred to as concentration polarization. Concentration polarization occurs when a voltage is applied in any electrolytic cell. Concentration polarization results because a thin layer of fluid in contact with the anode surface becomes depleted of chloride ions and forms what is referred to as a double layer. The double layer can be thought to provide a slight reverse voltage which opposes the current causing electrolysis. Thus, concentration polarization slows the desired electrolytic reaction. As concentration polarization continues, a point can be arrived at during which concentration polarization completely opposes the current applied by the external power supply 120. While concentration polarization is more pronounced at an anode, concentration polarization also occurs at a cathode.

While there is almost always some degree of concentration polarization at the surface of an electrode, the electrode assembly 122A reduces any undesirable consequences by allowing fluid to pass through the fluid passageway 125 to replenish the chloride ions and thus decrease the thickness of the depletion layer. It is to be understood that many different structures can function equivalently to the fluid passageway 125, including devices which provide mechanical agitation and structure to facilitate convection flow of the fluid. Those skilled in the art will appreciate that many different structures can perform the function of providing replenishing fluid flow to the surface of one or more electrodes.

Figure 4:
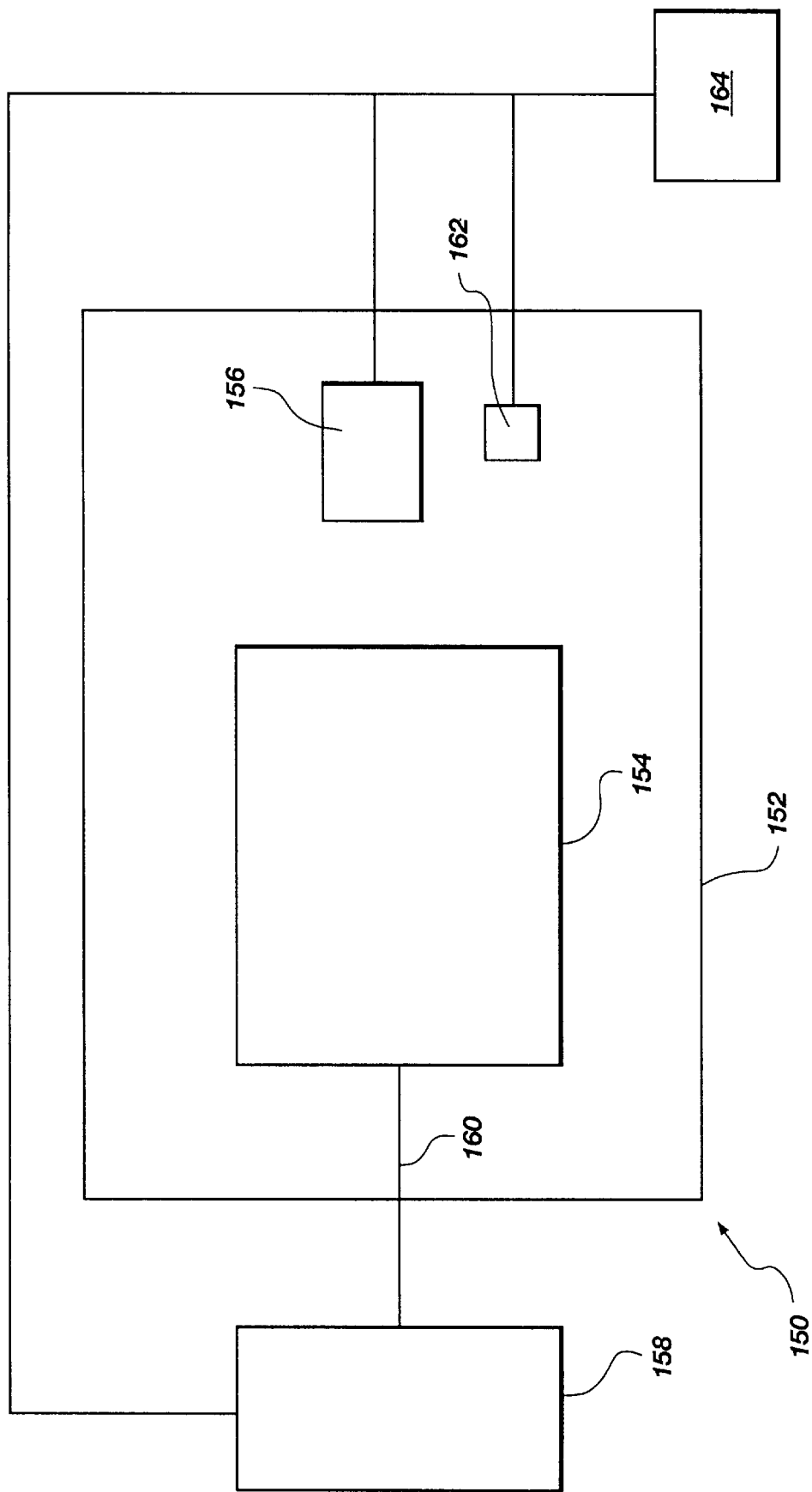
FIG. 4 is a block diagram of a second presently preferred embodiment of the present invention.

Reference will next be to FIG. 4 which is a block diagram of a second presently preferred embodiment, generally represented at 150, of the present invention. The embodiment represented in FIG. 4 is particularly adapted for treating large quantities of saline solution. Represented in FIG. 4 is a tank 152 in which the saline solution is electrolyzed. An electrode assembly 154 is provided in the tank and is preferably immersed into the solution. A power supply 158, capable of providing sufficient current at the proper voltage (as discussed earlier), is connected to the electrode assembly via a cable 160.

Also represented in FIG. 4 is a circulation device 156 which optionally functions to circulate the solution within the tank 152 and to replenish the solution within the tank 152 to the surfaces of the electrodes. A sensor 162 is also optionally provided to measure the progress of the electrolyzation of the solution in the tank 152, for example by measuring the pH of the solution. The sensor may preferably be an ion selective electrode which can be chosen from those available in the art. For example, one preferred ion selective electrode is available from Baxter which is sensitive to chlorine ($Cl_2$) accompanied by a Model 290A Portable pH/ISE meter which includes a RS232 port for exchange of data and control signals with other devices. It will be appreciated that many other types of sensors, for example other sensors which are sensitive to chlorine, ozone, and temperature, may also be included within the scope of the present invention. A control unit 164 is optionally provided to coordinate the operation of the power supply 158, the circulation device 156, and the sensor 162 in order to obtain the most efficient operation of the apparatus 150.

It will be appreciated that devices such as power supply 158, circulation device 158, sensor 162, and control unit 164 can be selected from sources in the industry and adapted for use with embodiments of the present invention by those skilled in the art using the information contained herein. In particular, the control unit 164 is preferably a digital microprocessor based device accompanied by appropriate interfaces all allowing for accurate control of the operation of the apparatus 150. It is also within the scope of the present invention to include structures to prevent contamination of the treated solution by contact with nonsterile surfaces and by airborne pathogens both during treatment and while the fluid is being transferred to the apparatus and being withdrawn from the apparatus.

Figure 5:
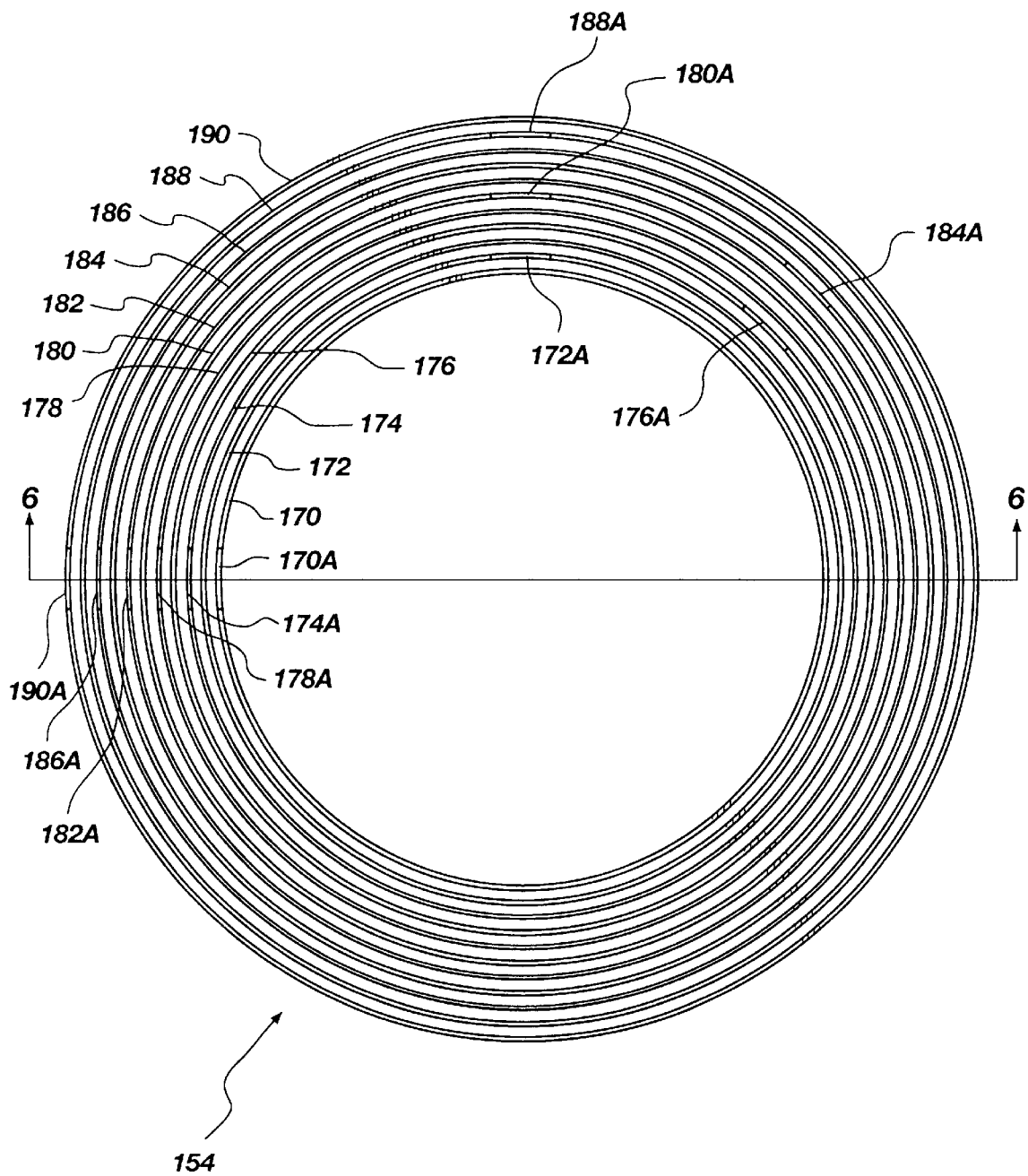
FIG. 5 is a top view of an electrode assembly preferred for use in the apparatus represented in FIG. 4.
Figure 6:
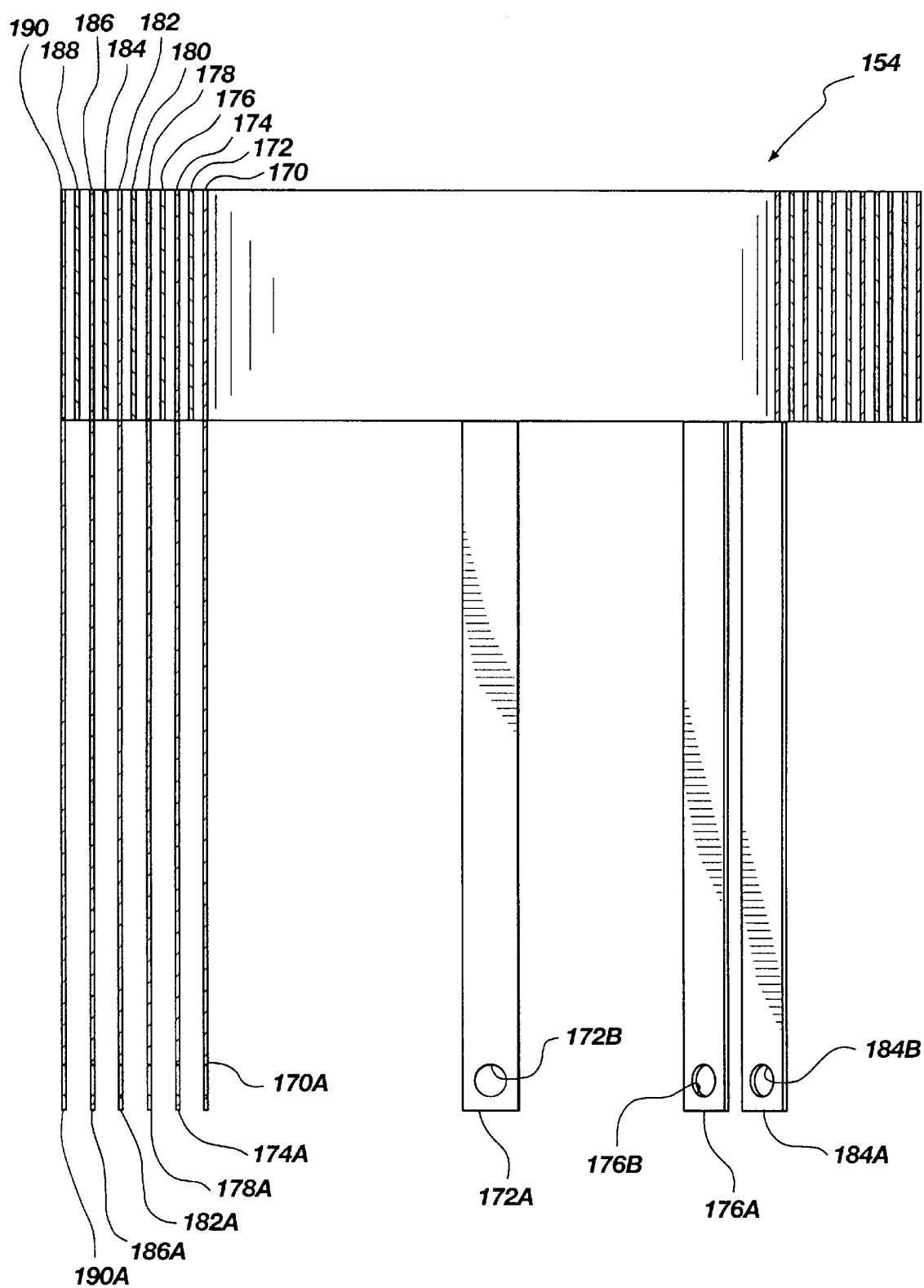
FIG. 6 is a cross sectional view taken along line 6—6 of FIG. 5.

Reference will next be made to FIGS. 5 and 6 which are a top view and a cross sectional view, respectively, of an electrode assembly, generally represented at 154, which is preferred for use in the apparatus represented in FIG. 4. As can be seen best in FIG. 5, the electrode assembly 154 includes a plurality of concentrically arranged anodes and cathodes. The cylindrical shape and concentric arrangement of the electrodes represented in FIG. 5 provides for the most efficient operation. The number of electrodes which are included can be selected according to the application of the apparatus. For example, the number of electrodes may be six, seven, eight, or the eleven represented in FIGS. 5 and 6, or more.

In FIG. 5, electrodes 170, 174, 178, 182, 186, and 190 preferably function as cathodes and are preferably fabricated in accordance with the principles set forth above in connection with the outer electrode represented at 126 in FIGS. 1–3. Furthermore, in FIG. 5 electrodes 172, 176, 180, 184, and 188 function as anodes and are preferably fabricated in accordance with the principles set forth above in connection with the inner electrode represented at 128 in FIGS. 1–3.

In the cross sectional side view of FIG. 6 a plurality of tabs extend from the cylindrical electrodes 170, 172, 174, 176, 178, 180, 182, 184, 186, and 190 to facilitate making electrical connections thereto. Provided below in Table A are the relationship between the tabs illustrated in FIG. 6 and the electrodes.

TABLE A

| Electrode | Tab | Function |
| --- | --- | --- |
| 170 | 170A | Cathode |
| 172 | 172A | Anode |
| 174 | 174A | Cathode |
| 176 | 176A | Anode |
| 178 | 178A | Cathode |
| 180 | 180A (Not illustrated in FIG. 6) | Anode |
| 182 | 182A | Cathode |
| 184 | 184A | Anode |
| 186 | 186A | Cathode |
| 188 | 188A (Not illustrated in FIG. 6) | Anode |
| 190 | 190A | Cathode |

Using the tabs 170A, 172A, 174A, 176A, 178A, 180A, 182A, 184A, 186A, 188A, and 190A, those skilled in the art can provide the necessary electrical connections to the electrodes 170, 172, 174, 176, 178, 180, 182, 184, 186, and 190. Those skilled in the art can also provide structures to prevent contact between the tabs and the fluid to be treated. Each of the tabs illustrated in FIG. 6 are provided with an aperture, such as those represented at 172B, 176B, and 184B, which receive a wiring connector which can be selected from those available in the industry.

While the apparatus described herein has many uses, the most preferred use of the apparatus represented in FIGS. 1–6 is subjecting sterile saline solution to electrolysis. The electrolyzed saline solution can then be used to treat a patient. The saline solution preferably has an initial concentration in the range from about 0.05% to about 10.0% NaCl, more preferably has an initial concentration in the range from about 0.1% to about 5.0% NaCl, and most preferably has an initial concentration of about 0.15% to about 1% NaCl. The dilute saline solution is subjected to electrolysis using the embodiments of the present invention at a voltage, current, and time to produce an appropriately electrolyzed solution as will be described shortly. It is presently preferred to carry out the electrolysis reaction at ambient temperatures. In one exemplary use of the described apparatus, a saline solution having an initial concentration of NaCl which was about one-fourth to full strength of normal or isotonic saline solution was used. According to *Taber's Cyclopedic Medical Dictionary*, E. A. Davis, Co. 1985 Ed., an "isotonic saline" is defined as a 0.16M NaCl solution or one containing approximately 0.95% NaCl; a "physiological salt solution" is defined as a sterile solution containing 0.85% NaCl and is considered isotonic to body fluids and a "normal saline solution;" thus, a 0.9% NaCl solution is considered isotonic to the body. Therefore, the terms "isotonic," "normal saline," "balanced saline," or "physiological fluid" are considered to be a saline solution containing in the range from about 0.85% to about 0.95% NaCl.

Preferably, the voltage used with the embodiments illustrated herein is not greater than about 30 volts. Utilizing a relatively lower voltage minimizes the production of undesirable products. The current values and the time the saline solution is subject to electrolysis, is determined by variables such as the surface area and efficiency of the particular electrode assembly and the volume and/or concentration of saline solution being electrolyzed. For electrode assemblies having a different surface area, greater volumes of saline solution, or higher concentrations of saline solutions, the voltage, current, or time may be higher and/or longer than might be otherwise used.

In accordance with the present invention, it is the generation of the desired concentration of ozone and active chlorine species which is important. Electrolyzation of the saline solution also results in other products of the electrolysis reaction including members selected from the group consisting of hydrogen, sodium and hydroxide ions. It will be appreciated that the interaction of the electrolysis products results in a solution containing bioactive atoms, radicals or ions selected from the group consisting of chlorine, ozone, hydroxide, hypochlorous acid, hypochlorite, peroxide, oxygen and perhaps others along with corresponding amounts of molecular hydrogen and sodium and hydrogen ions.

According to Faraday's laws of electrolysis, the amount of chemical change produced by a current is proportional to the quantity of electrons passed through the material. Also, the amounts of different substances liberated by a given quantity of electrons are proportional to the chemical equivalent weights of those substances. Therefore, to generate an electrolyzed saline having the desired concentrations of ozone and active chlorine species from saline solutions having a saline concentration of less than about 1.0%, voltage, current, and time parameters appropriate to the electrodes and solution are required to produce an electrolyzed solution containing in the range from about 5 to about 100 mg/L of ozone and a free chlorine content in the range from about 5 to about 300 ppm. More preferably, the treatment produces an electrolyzed solution containing in the range from about 10 to about 50 mg/L of ozone and a free chlorine content in the range from about 10 to about 100 ppm. Most preferably, the treatment produces an electrolyzed solution containing in the range from about 20 to about 30 mg/L of ozone and a free chlorine content in the range from about 20 to about 60 ppm. For in vitro use these solutions can be utilized without further modification or they can be adjusted as desired with saline or other solutions. Prior to in vivo use, the resulting solution may be adjusted or balanced to an isotonic saline concentration with sufficient hypertonic saline, e.g., 5% hypertonic saline solution.

In general, the electrolyzed solutions produced using the apparatus described herein, which are referred to as microbicidal solutions, will have an ozone content in the range from about 5 to about 100 mg/L and an active chlorine species content in the range from about 5 to about 300 ppm. More preferably the ozone content will be in the range from about 5 to about 30 mg/L and the active chlorine species content will be in the range from about 10 to about 100 ppm. Most preferably the ozone content will be in the range from about 9 to about 15 mg/L and the active species content will be in the range from about 10 to about 80 ppm. By active chlorine species is meant the total chlorine concentration attributable to chlorine content detectable by a chlorine ion selective electrode and will be selected from the group consisting of chlorine, hypochlorous acid and hypochlorite ions or moieties.

The pH of the solution is preferably in the range from about 7.2 to about 7.6 and, when used for intravenous administration, most preferably in the range from about 7.35 to about 7.45 which is the pH range of human blood. An effective amount of the resulting balanced microbicidal saline solution is administered by appropriate modes, e.g., intravenously, orally, vaginally or rectally and may vary greatly according to the mode of administration, condition being treated, the size of the warm-blooded animal, etc.

Particular dosages and methods of administration, as well as additional components to be administered, can be determined by those skilled in the art using the information set forth herein and set forth in the U.S. patent documents previously incorporated herein by reference. As explained in the cited U.S. patent documents, although it is known that electrolyzed saline solutions possess in vitro microbicidal activity it has long been thought that components in the electrolyzed solution, such as ozone and chlorine, are toxic to warm blooded animals and should not be utilized for in vivo administration. It has now been found, however, that saline solutions, which have been subjected to electrolysis to produce finite amounts of ozone and active chlorine products, can be injected into the vascular system to create a reaction to assist in the removal, passivation, or destruction of a toxin.

One preferred method for arriving at a preferred end product using the apparatus illustrated in FIGS. 1–3 will now be described. An approximately 0.33% (about one third physiologically normal) saline solution is placed in the fluid vessel 116 (FIG. 1) and the apparatus is operated for about 5 to 15 minutes with a voltage between the electrodes being maintained in the range from about 10 volts to about 20 volts with a current flow maintained in the range from about 5 to about 20 amps.

As another example of the use of the embodiment of FIGS. 1–3, a 0.225% saline solution is subjected to a current of 3 amperes at 20 volts (DC) for a period of three minutes. A 17 ml portion of this electrolyzed solution is aseptically diluted with 3 mls of a sterile 5% saline resulting in a finished isotonic electrolyzed saline having an active ozone content of 12±2 mg/L and an active chlorine species content of 60±4 ppm at a pH of 7.4.

As yet another example of the use of the embodiment of FIGS. 1–3, a 0.225% saline solution is subjected to a current under 5 amperes at a voltage under 30 volts (DC) for a period of not more than five minutes. The resulting electrolyzed solution is aseptically diluted with enough sterile 5% saline to result in a finished isotonic electrolyzed saline having an active ozone content of 26±0.8 mg/L and an active chlorine species content of 40±2 ppm at a pH of 7.4.

It will be appreciated that the low voltages used in accordance with the present invention are preferably not greater than fifty (50) volts DC or an equivalent value if other than direct current is used. More preferably, the voltages used in accordance with the present invention are not more than about forty (40) volts DC or most preferably not more than about thirty (30) volts DC. The use of relatively low voltages avoids the problem of production of undesirable products in the fluid which can result when higher voltages are used. In accordance with the present invention, the close spacing of the electrodes facilitates the use of low voltages. The embodiments of the present invention also preferably provide that the supplied voltage can be adjusted to facilitate efficient electrolyzation of the fluid. The embodiments of the present invention may be able to provide relatively high voltages but the benefits of the present invention are still obtained by adjusting the value of the applied voltage in a range below the relatively low, preferred voltages described herein.

In another example, the embodiment of FIGS. 1–3 was used to effectively carry out electrolysis in saline solutions up to about 1% in concentration, namely, carried out at saline concentrations of 0.3, 0.6 and 0.9%, respectively. The active chlorine species (Cl$_2$) and ozone (O$_3$) contents were measured and are provided in Table B.

TABLE B

Cl$_2$ and O$_3$ Content from Salines at Varying Concentrations

| Initial Saline Concentration (% NaCl) | Cl$_2$ Concentration (ppm) | O$_3$ Concentration (mg/ml) |
|---|---|---|
| 0.3 | 129 | 21.8 |
| 0.6 | 161 | 26.6 |
| 0.9 | 168 | 28.0 |

As can be seen from Table B, the resulting electrolyzed saline solution includes active components which are within the parameters required for effective treatment of warm blooded animals.

It will be appreciated that the features of the present invention, including the close electrode spacing, the low voltage used, and/or the materials used to fabricate the electrodes, result in an apparatus which provides unexpectedly better results than the previously available devices and schemes.

Figure 7:
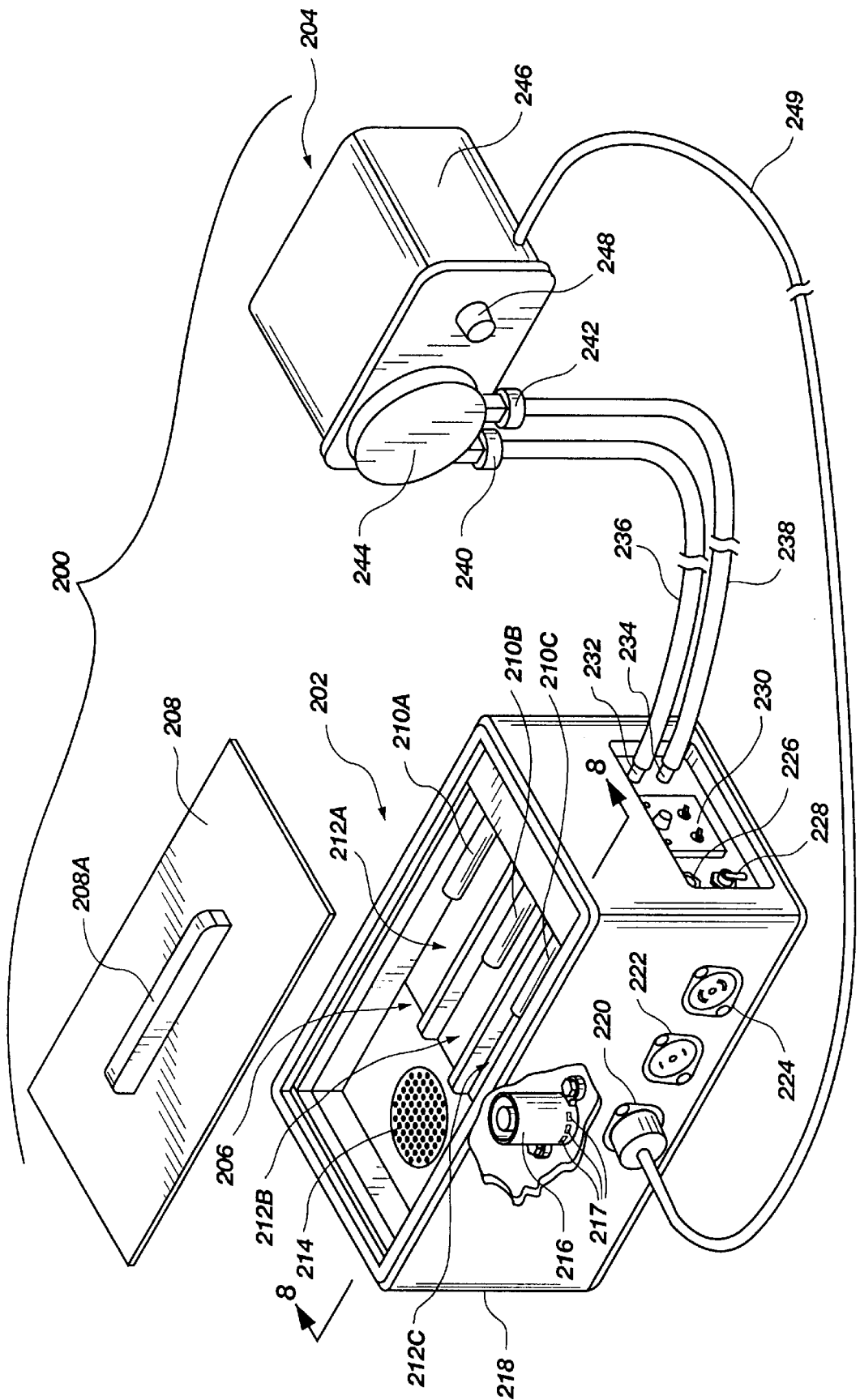
FIG. 7 is a perspective view of a third presently preferred embodiment for electrolyzing a fluid and using such electrolyzed fluid to sterilize the surfaces of medical and dental instruments.
Figure 8:
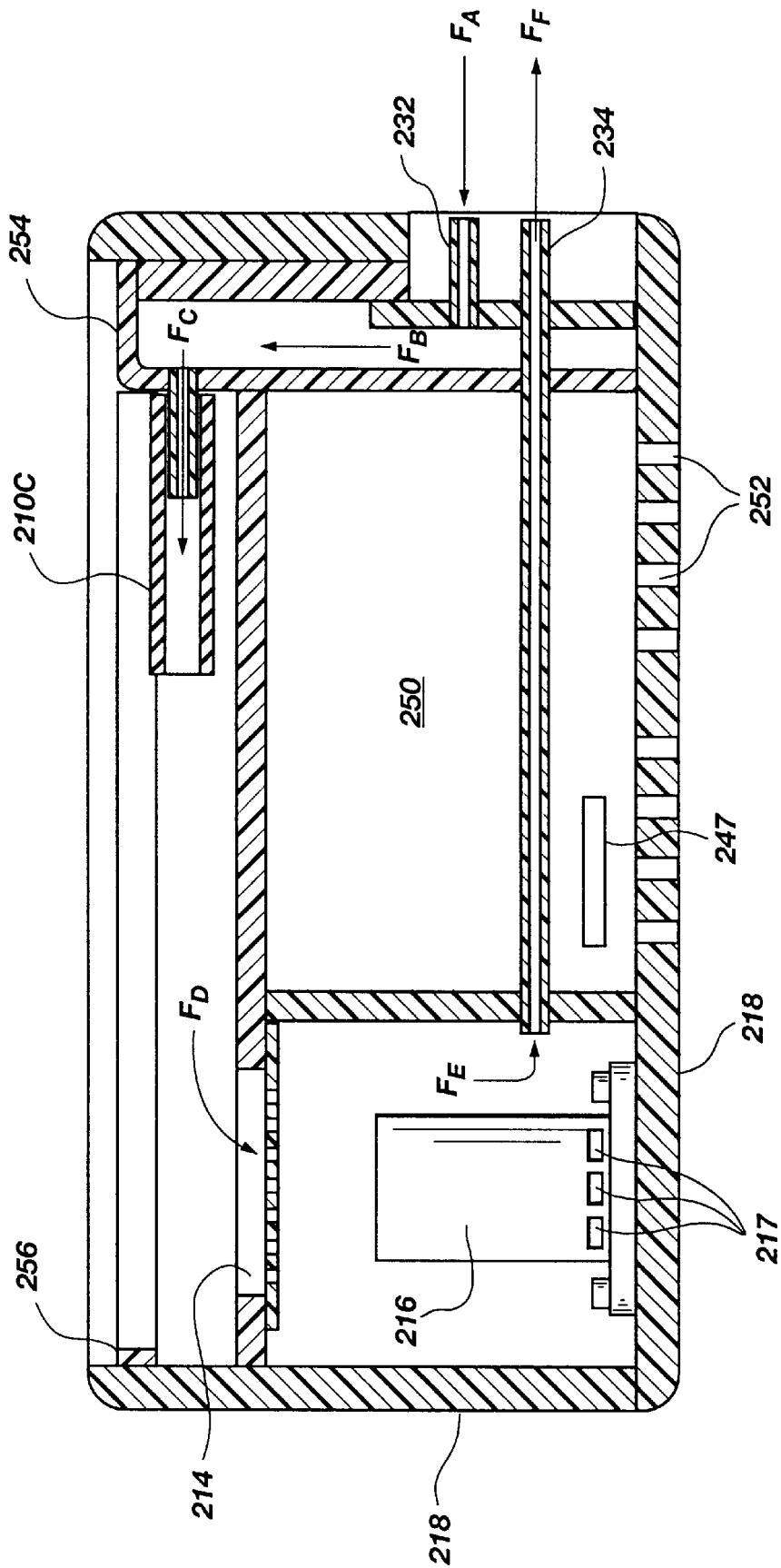
FIG. 8 is a cross sectional view of the third embodiment taken along line 8—8 of FIG. 7.
Figure 9:
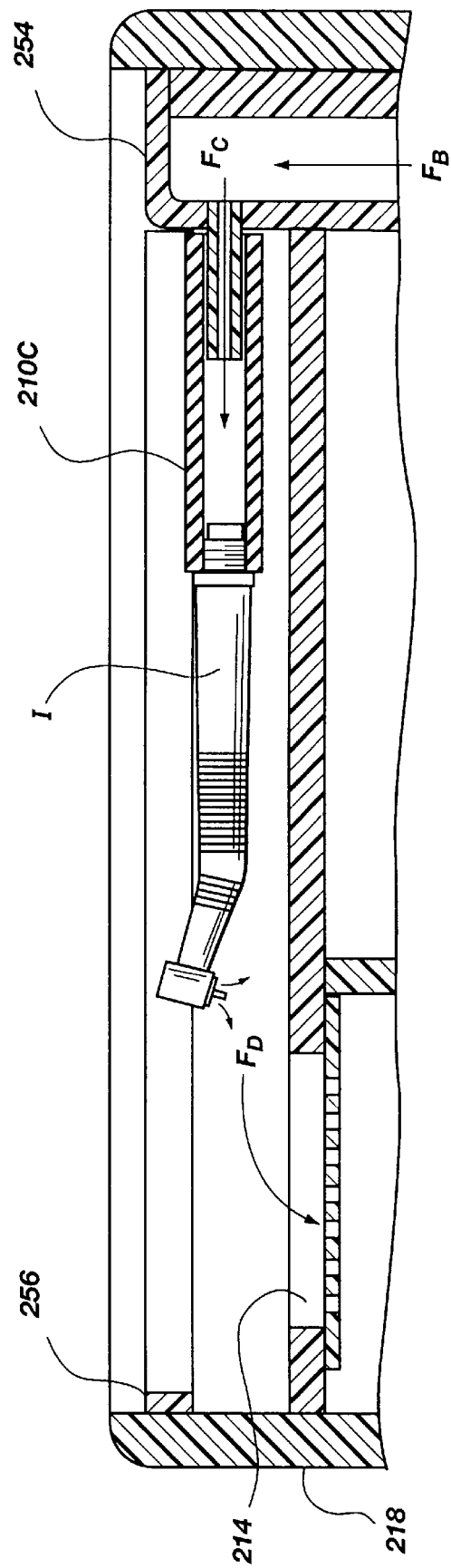
FIG. 9 is a detailed cross sectional view of a portion of the third embodiment represented in FIG. 7.

Reference will next be made to FIGS. 7–9 which illustrate one preferred embodiment of the present invention particularly suited for disinfecting and/or sterilizing health care equipment and which is uniquely suited for sterilizing medical and dental instruments. The description of the embodiment of FIGS. 7–9 will use the exemplary application of sterilizing dental drill handpieces (as represented in FIG. 9). It is to be understood that the sterilization of dental drill handpieces is merely exemplary of the many instruments which can be sterilized using embodiments of the present invention. It is also to be understood that many different embodiments of the present invention, in addition to the one represented in FIGS. 7–9 can be fabricated in accordance with the present invention.

Very serious consequences can arise from use of an disinfectant or sterilant. Patient-to-patient cross-contamination may occur when microbes are introduced into the medical or dental environment or onto or into medical or dental instruments following their use in certain medical or dental procedures. Numerous forms of microorganisms present this potential. Depending upon the particular microorganism and the susceptibility of a subsequent patient exposed to the microorganism, the consequences of cross-contamination from patient-to-patient may be deadly. The risk of any infection, including procedure-related, cross-contamination-caused infection, is higher for patients with impaired immune systems (such as AIDS or cancer patients). For example, even if, in testing or actual use, a sterilant or disinfectant successfully killed the extremely fragile HIV or AIDS virus, it might not be able to kill other more durable microorganisms (including spores). If incomplete microorganism kill occurs, there is a high possibility that an immuno-suppressed patient exposed to an improperly sterilized instrument may contract an opportunistic infection, which may be fatal.

Doctors, dentists, and other users must rely on a sterilization process to be effective; there is no margin of error. In the ordinary course of medical or dental practice, ineffective sterilization cannot be detected and could result in the use of a contaminated instrument by a medical or dental professional. The use of a contaminated instrument poses a risk of infection that would not exist if a properly sterilized instrument were used instead.

As will be appreciated by those familiar with dental practices, the sterilization of dental drill handpieces presents particularly challenging circumstances. Dental drill handpieces are exposed to a patient's blood and tissue which presents the danger of cross infection from one patient to another patient. More challenging is the fact that dental drill handpieces contain small mechanical parts which are exposed to the patient's blood and tissue and present numerous small cracks, cavities, and openings in which tissue and blood can attach. Thus, dental drill handpieces pose a challenge to providing clean and sterile equipment to a patient. Many dental patients are particularly questioning the infection control practices of their dental practitioners and are demanding that suitable practices be implemented. In order to assure their patients of the greatest infection control possible, some dental practitioners have even resorted to the expensive procedure of using single use, disposable dental drill handpieces.

According to accepted standards in the industry, two levels of destruction of microbes on inanimate objects are recognized: Sterilization is defined as the destruction of all microbial life, including bacterial spores; Disinfection is defined as the elimination of nearly all recognized pathogenic microorganisms, but not necessarily all microbial forms (e.g., bacterial spores). Disinfection does not ensure overkill and lacks the margin of safety achieved by sterilization.

Sterilization by definition is a process that is lethal to all microbial life, including bacterial spores. The U.S. Department of Health and Human Services Centers for Disease Control and Prevention uses a classification scheme in which medical and dental instruments and items for patient care are divided into categories on the basis of the risk of infection involved in the use of these items, as follows: (a) Critical items present a high risk of infection if the item is contaminated with any microorganism, including bacterial spores. Items that enter the vascular system or sterile tissue, such as surgical instruments, dental surgical instruments, implants, cardiac or urinary catheters, and hypodermic needles, are critical items. To avoid the risk of infection, these items must be sterilized, including the destruction of bacteria spores. (b) Semi-critical items are objects that contact intact mucous membranes (e.g., the mouth, nose, or rectum) but will not ordinarily penetrate the blood barrier or enter other ordinarily sterile areas of the body. Examples of semi-critical items are dental mirrors and aspirators, respiratory therapy and anaesthesia equipment, endoscopes, and diaphragm-fitting rings. Intact mucous membranes are generally resistant to infection by common bacterial spores, but are susceptible to infection by other organisms such as tuberculosis bacilli and viruses. Accordingly, semi-critical items must be free of all microorganisms, except for bacterial spores (to provide added assurance to patients, it is very desirable that these semi-critical items also be sterilized). (c) Non-critical items which contact intact skin and include stethoscopes, blood pressure cuffs, bed pans, and linens. Intact skin is an effective barrier to most microorganisms and simple disinfection of non-critical items is sufficient.

Standards of practice for infection control have been established and accepted by the medical and dental community. Examples include the Center for Disease Control and Prevention Guideline for Hospital Environmental Control, 1981 and revised in 1985, Association for Practitioners in Infection Control Guideline for Selection and Use of Disinfectants, 1990, and Infection Control in the Dental Environment, issued jointly by the Departments of Veterans Affairs and Health and Human Services and the American Dental Association in 1990. All of these guidelines recommend that instruments or other items used for patient care be thoroughly cleaned before they are sterilized. Thorough cleansing can remove contaminating microorganisms and organic matter. Residual organic matter (such as blood or saliva) not only adds to the microbial load, but interferes with the disinfection process by preventing the antimicrobial agent from reaching the surface of the instrument and by directly reacting with the antimicrobial agent. It is recognized by those skilled in the art that the procedures of cleaning and sterilization of medical and dental instruments has generally been a time consuming and sometimes laborious and burdensome process, particularly in the case of a small medical or dental practice, which must be carried out in order to assure patient safety.

It is well known that steam sterilization for provides the most reliable sterilization. Importantly, in the case of dental drill handpieces, which include high speed turbine fiber optic components, are fragile and repeated steam sterilization in an autoclave greatly reduces the lifetime of these instruments. Moreover, steam serialization in an autoclave can be expensive and burdensome to carry out in a small medical or dental practice.

As known to those skilled in the art, standards have been established to determine if a method of sterilization is effective. Such standards generally require that bacterial spores must be effectively destroyed. Examples of such standards are found in 40 C.F.R. 158.640 (1995) which is now incorporated herein by reference.

One test for sterilization requires that the sterilization process to kill bacterial spores. Spores of one of two spore-forming microorganisms are generally used, for example *Bacillus subtilis* and *Bacillus stearothermophilus*. Spores are the dormant state of microorganisms, typically bacteria, which exhibit a lack of biosynthetic activity, reduced respiratory activity, and are resistance to heat, radiation, and various chemical agents. Spores are the most hardy and resistant to destruction forms of life. Accordingly, spores are used to determine the efficacy of a sterilization process; Any process which is capable of killing spores is judged to be capable of killing any other form of microbial life. If microorganisms are not killed, they may contaminate medical or dental environments and instruments. If microorganisms on instruments are not killed and remain viable, they may cause serious infection upon contact with a patient.

For a sterilization process under test to provide complete sterilization, the process must kill all spores. No failures are permitted. The testing protocol should simulate real world conditions. First, the testing protocol requires that the spores from microorganisms, for example, *Bacillus subtilis* and *Bacillus stearothermophilus,* be cultured. Objects are then inoculated with the spores. For example, a medical instrument itself can be inoculated with the spores or items such glazed porcelain cylinders and silk surgical suture loops which act as "carriers." The instruments or carriers are then subjected to the sterilization process.

In order to determine if the spores have been completely killed, the inoculated items are transferred to a medium that permits spore growth and observed for a period of 21 days. Any items which does not exhibit growth after 21 days can be heat shocked to ensure that no viable spores remain. Heat shock is a process whereby an inoculated item is placed in a growth medium which is heated to 80 degrees Celsius in a final effort to determine whether any living spores remain. The heat shocked items are rechecked for growth after 72 hours. Lack of growth after this stage of testing indicates that the spores on the inoculated items have been completely killed by the sterilization process being tested.

With an understanding of the stringent requirements placed on sterilization processes, a description of the system illustrated in FIGS. 7–9 will be provided. Referring first to FIG. 7, a sterilization system 200 is represented. The sterilization system 200 includes a serialization unit, generally indicated at 202, and a pump unit, generally indicated at 204, which in the illustrated embodiment is separated from the sterilization unit 202 but can be incorporated into housing 218 of the sterilization unit 202 in other embodiments of the invention. The housing 218 is preferably fabricated from a material which is electrically insulative and which resists corrosion.

As can be seen in the cut away portion of the housing 218, an electrode assembly 216 is provided within the housing 218. The electrode assembly 216 is connected to a power supply, such as the power supply 102 (FIG. 1) which has been modified to output power through a connector which mates with receptacle 224 provided on the housing 218. The power supply used in the embodiment of the invention represented in FIGS. 7–9 is preferably operated similarly to the power supplies described earlier herein with the understanding that the voltage and current values used may be different since the resulting electrolyzed solution is not for in vivo administration and since the chlorine and ozone content must be sufficient to act as a sporicide. The electrode assembly 216 is electrically coupled to the receptacle 224 and receives the voltage and current needed to provide electrolyzed saline solution which has the desired antimicrobial, and/or sporicidal, action. In other embodiments of the invention it is preferred to provide a power supply within the housing 218.

The electrode assembly 216 is provided with fluid passageways 217 through which fluid can flow to improve the flow of fresh solution over the surfaces of the anode and cathode in the electrode assembly 216. The fluid passageways 217 are preferably fabricated in accordance with the explanation provided in connection with FIGS. 3A and 3B.

The cross sectional view of FIG. 8 will now be referred to concurrently with the perspective view of FIG. 7 to improve the clarity of the following description. As seen best in FIG. 7, a holding tray, generally indicated at 206, is provided to hold medical and dental instruments (one of which is represented at I in FIG. 9). Three instrument holders 210A–C, which in the illustrated embodiment are preferably lengths of flexible tubing, are positioned in channels 212A–C. The medical or dental instruments to be sterilized are preferably placed in the holding tray 206 or within the channels 212A–C if the instruments are not inserted into the instrument holders 210A–C. It will be appreciated that embodiments of the present invention can accommodate many more, and different types, of medical/dental instruments than specifically described herein. A screen 214 separates the holding tray 206 from the electrode assembly 216 but allows fluid flow therebetween.

The circulation of the electrolyzed saline solution is best described by reference to FIG. 8. FIG. 8 provides a cross sectional view of the internal construction of the housing 218 which facilitates the circulation of the electrolyzed saline solution. As shown in FIG. 8, electrolyzed saline solution is pumped in the direction of arrow $F_A$ into an inlet. The electrolyzed saline solution courses in the direction of arrows $F_B$ and $F_C$ and out through the instrument holder 210C. After passing over and/or through the instrument (see FIG. 9), the electrolyzed saline solution flows through the screen 214 in the direction of arrow $F_D$ where it is treated again by the electrode assembly 216. The electrolyzed saline solution leaves the vicinity of the electrode assembly in the direction of arrow $F_E$ to an outlet 234 where it returns to the pump unit 214 in the direction of arrow $F_F$.

The circulation of electrolyzed saline solution not only provides that freshly electrolyzed saline solution is applied to the instrument but the flow of solution also provides removal of debris, such as patient's blood and tissue, which might otherwise adhere to the instrument (see FIG. 9) and be transferred to another patient or which reduces the efficiency of the sterilization process. It is to be understood that the structure of the housing of various embodiments of the present invention will differ greatly from that illustrated in FIGS. 7–9 and all such embodiments are intended to fall within the scope of the present invention. As seen in the cross sectional view of FIG. 8, an interior compartment 250, with vent holes 252 and a fan 247, in which electrical components and other components can be placed is represented.

Referring again to the perspective view provided in FIG. 7, a lid 208, provided with a handle 208A, is placed over the holding tray 206 to prevent foreign objects from falling into the holding tray 206. The lid 208 rests on shelves 256 and 254 when in place over the holding tray 206. A receptacle 222 is provided to convey electrical power to a pump control unit 230. A pump switch 226 is provided apply power which is received from the receptacle 222 to the pump control unit 230.

The pump control unit 230 provides interval timing for the operation of the pump unit 204 and provides for overall timing of the operation of the pump unit 204. One example of a device which can function as a pump control unit is a 48K series timer available from Amerace Electronic Components under the AGASTAT® trademark. The inlet 232 and the outlet 234 are connected to the pump unit 204 via hoses 236 and 238, respectively. One exemplary device which can be used as the pump unit 204 is a peristaltic type pump, for example, one available from Blue White Industries under the FLEXFLO® mark. While many different types of pumps and other devices can be used within the scope of the present invention, the peristaltic type pump provides advantages of accurate flow rates and sufficient pressure to remove any occlusion present in an instrument being sterilized. It is also preferred that a filter device be included within the flow of electrolyzed saline solution. Depending upon the end use of an embodiment of the present invention, a pump device can be selected which provides suitable performance.

The preferred pump unit 204 includes first and second ports 240 and 242 which connect to the hoses 236 and 238, respectively, and convey the electrolyzed saline solution to the pump apparatus which is positioned under the pump cover 244. A housing 246 contains a motor which receives electrical power from the cable 249 which is connected to the pump control unit 230 via the receptacle 220. A switch 248 is also provided on the pump unit 204. A circuit breaker 228 is provided to protect against excess current flow.

Reference will next be made to FIG. 9 which is a detailed cross sectional view of the holding tray 206 with a dental drill handpiece (represented at I) having one of its ends inserted into the instrument holder 210C. As is known in the industry, the dental drill handpiece includes internal conduits which convey pressurized air for operation of a turbine to rotate the drill, internal conduits for conveying water to the drill site, and a fiber optic bundle which is used to convey light to the drill site. During sterilization, the end of the dental drill handpiece I is inserted into the instrument holder 210C so that electrolyzed saline solution is directed into these conduits. The preferred flexible tubing functioning as an instrument holder 210C forms a loose seal about the end of the instrument so that some electrolyzed saline solution is forced through the conduits and some passes over the exterior of the instrument. This results in the instrument being both bathed in the electrolyzed saline solution and the internal conduits within the instrument being cleaned and sterilized. Each of the conduits inside of the dental drill handpiece, as well as other crevices and depressions on the dental drill handpiece, collect debris, including a patient's blood and tissue which is removed by the flow of the electrolyzed saline solution provided by the embodiments of the present invention.

Importantly, the dental drill handpieces are damaged by the high temperature experienced in an autoclave. It is estimated that in the United States each dentist spends an average of $17,000 on the repair of dental drill handpieces, with sterilization using an autoclave necessitating repairs to the handpieces much sooner than would otherwise be necessary. Moreover, alternative sterilization techniques, for example using the poisonous gas ethylene oxide, are not cost effective alternatives for a small dental or medical practice. Advantageously, the present invention effectively sterilizes dental drill handpieces substantially at, or just slightly above, room temperature without causing damage which occurs when an autoclave is used to sterilize an instrument. It is to be understood that temperatures much above room temperature, for example 80 degrees Celsius, but below 100 degrees Celsius often promote microbial growth. Thus, the present invention beneficially operates at a temperature below 80 degrees Celsius, more preferably operates with the electrolyzed saline solution at the instrument having a temperature below 60 degrees Celsius, and most preferably at a temperature below 40 degrees Celsius or below 30 degrees Celsius.

It is to be understood that many different health care instruments in addition to dental drill handpieces can be sterilized using embodiments of the present invention. Embodiments of the present invention effectively kill spores of *Bacillus subtilis* and *Bacillus stearothermophilus*. The embodiments of the present invention are effective to kill such spores even when the instrument, for example the dental drill handpiece, itself is inoculated with such spores and then treated using an embodiment of the present invention. For example, an embodiment of the present invention, using a 1% NaCl solution which is electrolyzed using a current flow of 15 amperes, with the voltage being adjusted around 22 volts to maintain the current flow, effectively kills spores of *Bacillus stearothermophilus* and *Bacillus subtilis*. It will be appreciated that when using the apparatus of the present invention to sterilize or disinfect instruments, the voltage and current values used to electrolyze the saline solution can be greater than the values used when producing electrolyzed saline solution for in vivo administration. For example, voltages between the electrodes can be maintained in the range from about 10 volts to about 60 volts with a current flow maintained in the range from about 1 to about 40 amperes.

From the foregoing, it will be appreciated that many different embodiments of the present invention can be arrived at using the information set forth above. Reference will next be made to FIGS. 10A–D which represent a fourth presently preferred embodiment of the present invention which is suited for sterilizing a variety of items, and in particular dental instruments. For example, the embodiments of the present invention can be utilized to sterilize a variety of laboratory and clinical equipment, including glassware, pipettes, micro titter trays, flasks, tissue containers, cell harvesters, petri dishes, test tubes, and the like. Moreover, embodiments of the present invention have particular applicability in disinfecting and sterilizing food products, such as eggs, beef (both beef carcasses and portions), and poultry (both poultry carcasses and portions), which undergo processing and which are known on occasion to harbor harmful microorganisms. As described above, the present invention is particularly useful to sterilize items, such as many plastic items, which cannot resist the temperatures or chemicals which are commonly used to sterilize items used in laboratories and health care settings. As discussed above, the present invention can be used to treat biological fluids and materials.

Using the present invention, electrolyzed saline solution can also be used in vaccine development. Electrolyzed saline in accordance with the present invention is particularly suited for removing infectivity, while retaining immunogenicity, of a vaccine preparation. Use of the electrolyzed saline solution in accordance with the present invention provides vaccine processing with the absence of any microbial contaminants in the vaccine preparation.

All of mentioned items can be readily sterilized using the apparatus described herein or those skilled in the art can readily make modifications to provide efficient sterilization of such items in accordance with the present invention.

Figure 10A:
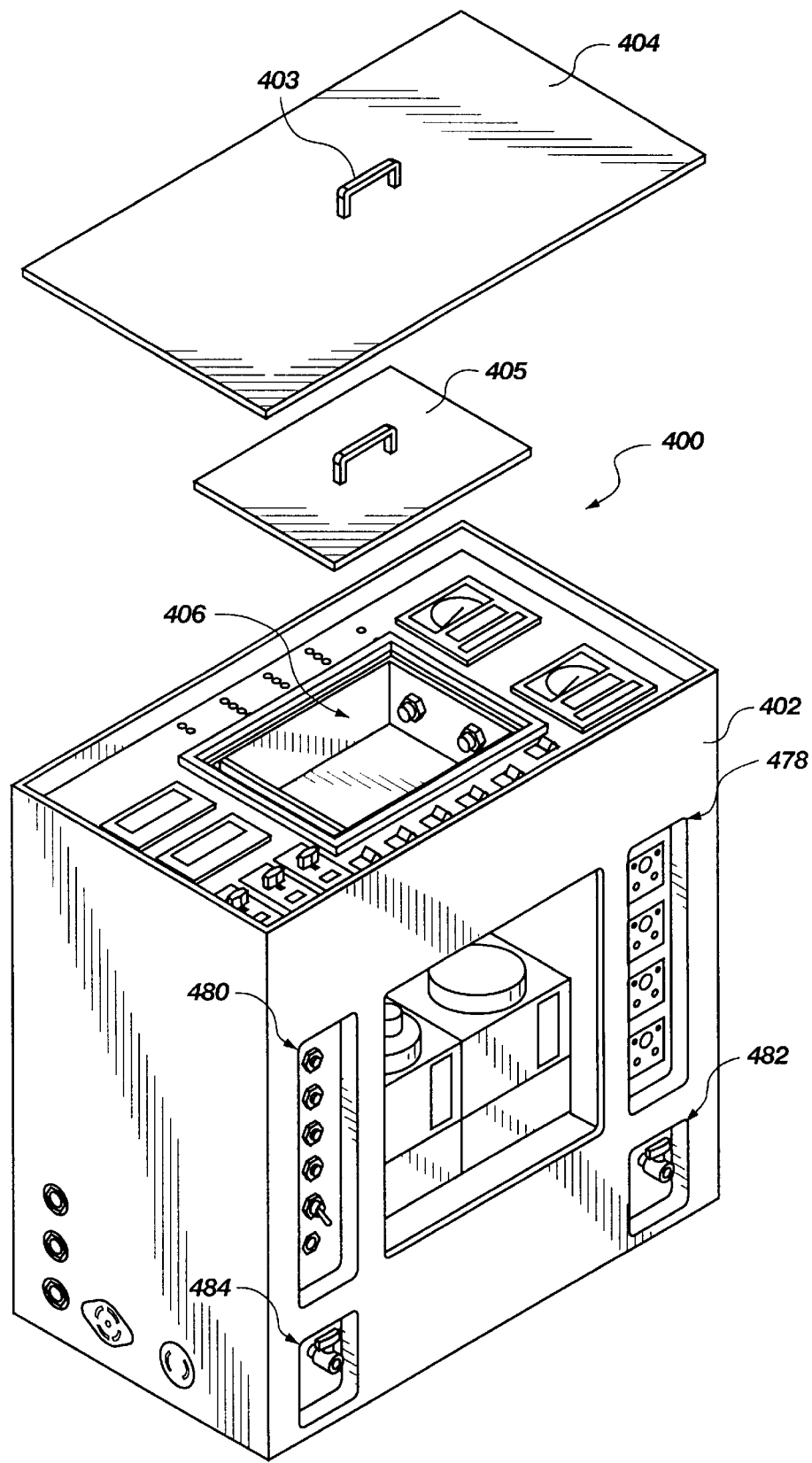
FIG. 10A is a perspective view of a fourth presently preferred embodiment of the present invention particularly adapted for automatically sterilizing various items.

Reference will next be made to FIG. 10A which is a perspective view of a fourth presently preferred embodiment of the present invention which will be referred to herein as an automatic sterilizer, generally indicated at 400. The automatic sterilizer 400 includes a housing 402, which is preferably fabricated from a plastic material well-known in the art. A lid 404 having a handle 403 is provided to cover the automatic sterilizer 400. A sterilizing chamber, generally indicated at 406, receives items to be sterilized. The sterilizing chamber 406 is fabricated from a material which is not degraded by the electrolyzed saline solution which is held therein. A lid 404, including a handle 403, is provided to cover the sterilizing chamber 406. It is to be appreciated that the embodiment represented in FIGS. 10A–D can be adapted to particularly sterilize many different types of items and also to simultaneously sterilize a greater or lesser number of items than are explicitly described herein. As will now be described, the automatic sterilizer 400 provides efficient sterilization of items, including medical and dental equipment.

Figure 10B:
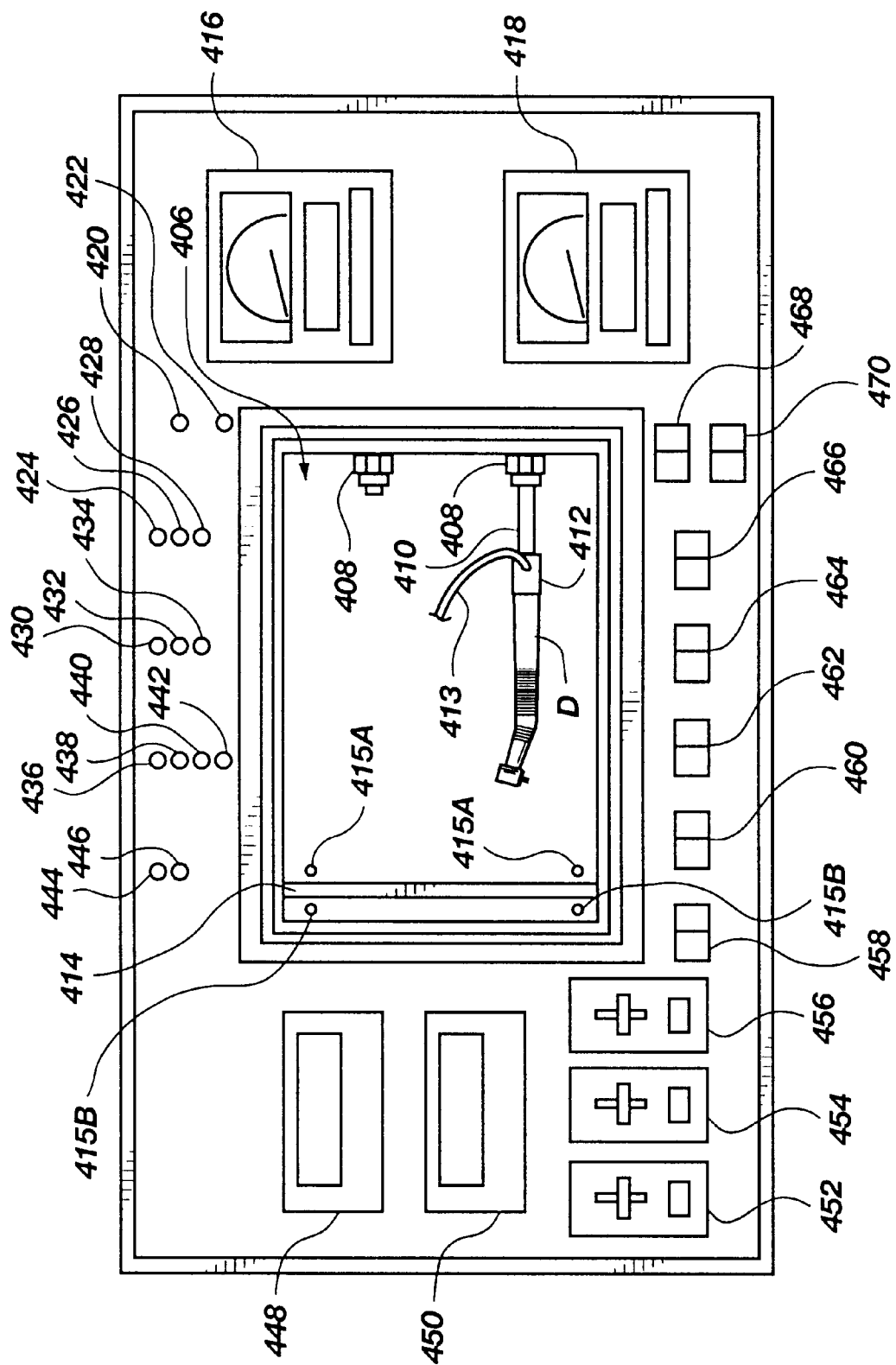
FIG. 10B is a top view of the fourth embodiment represented in FIG. 10A.

Reference will next be made to FIG. 10B which is a top view of the fourth presently embodiment of the present invention represented in FIG. 10A. Represented in FIG. 10B is a dental drill handpiece D which is positioned in the sterilizing chamber 406. A pair of connectors 408 communicate electrolyzed saline solution with the sterilizing chamber 406 and the item to be sterilized, an example of which is the dental drill handpiece D. The dental drill handpiece D is attached to the connector 408 via a tube 410 and a coupler 412. The coupler 412 is adapted to make a secure coupling to whatever dental drill handpiece D is to be sterilized, including couplings to internal intake and exhaust conduits for the turbine air, water, and air within the dental drill handpiece D. An exhaust tube 413 is also provided on the coupler 412.

The exhaust tube 413 is positioned so that it receives fluid (electrolyzed saline or sterile water) which has passed through the turbine portion of the dental drill handpiece D. In accordance with the present invention, injecting fluid into the air intake conduit of the dental drill handpiece D will cause the turbine contained therein to rotate. Controlling the rotation of the turbine provides more efficient cleaning and sterilizing of the dental drill handpiece. More information regarding the benefits of controlling the rotation of the turbine during cleaning will be discussed shortly. It is to be appreciated that it is within the scope of the present invention to also sterilize dental drill handpieces without any rotation of the turbine contained therein.

As indicated by the representation of the automatic sterilizer 400 provided in FIG. 10B, the exterior surface of the dental drill handpiece D (or other item to be sterilized) is bathed in the appropriate sterilizing solution. A pair of drain ports 415A are provided which return the fluid (electrolyzed saline or sterile water) to the appropriate container upon command, as will be described shortly. As the electrolyzed saline solution is recirculated (via a pump or vacuum, not represented in FIG. 10B), the user monitors the temperature and pH of the sterilizing solution and adjustments can be made as necessary.

A weir 414 is provided within the sterilizing chamber 406 to help maintain the volume of electrolyzed saline solution within the sterilizing chamber 406 at the desired level and to ensure that further mixing of the solution occurs as the fluid cascades over the weir and is recirculated via drain ports 415B (which are operated using a pump or vacuum as in the case of drain ports 415A). The automatic sterilizer 400 preferably includes a vacuum pump, or can be connected to an external vacuum source as is commonly available in dental and medical facilities, and is used to drain fluids rapidly, if necessary. The automatic sterilizer 400 represented in FIG. 10B includes sensors to determine the level of the fluid in the sterilizing chamber 406 and to drain fluid if a maximum level is exceeded.

Represented in FIG. 10B are a number of controls and indicators which interface with the internal components of the automatic sterilizer 400, all of which can be readily selected and arranged by one skilled in the art using the information provided herein. Provided in Table C is a description of the controls and indicators represented in FIG. 10B and their function.

TABLE C

| Control/ Indicator | Function | Exemplary Preferred Components |
|---|---|---|
| 416 | pH and Temperature Meter (with analog and digital displays) | Mfg. Signet pH Electrodes +GF+Signet 2714 Part # 3-2714 Description Flat pH electrode Preamplifier +GF+Signet 2720 Part # 3-2720 Description Preamplifier ¾ in. FNPT pH/ORP Monitor +GF+Signet 5700 Part # 3-5700 Description 5700 pH/ORP Monitor |
| 418 | Flow Meter (with analog and digital displays) | Micro Flow Sensor +GF+Signet 2000 Part # Description Micro Flow Sensor Flow Monitor |

TABLE C-continued

| Control/Indicator | Function | Exemplary Preferred Components |
|---|---|---|
| | | +GF+Signet 5500 Part # 3-5500 Description 5500 Flow Monitor |
| 420 | Pre Clean Drain Indicator | Panel Mounted LED |
| 422 | Post Clean Drain Indicator | Panel Mounted LED |
| 424 | Sterilizing Cycle Indicator - Start | Panel Mounted LED |
| 426 | Sterilizing Cycle Indicator - Finish | Panel Mounted LED |
| 428 | Sterilizing Cycle Indicator - Aborted | Panel Mounted LED |
| 430 | Post Cleaner Cycle Indicator - Start | Panel Mounted LED |
| 432 | Post Cleaner Cycle Indicator - Finish | Panel Mounted LED |
| 434 | Post Cleaner Cycle Indicator - Low Level | Panel Mounted LED |
| 436 | Pre Clean Cycle Indicator - Start | Panel Mounted LED |
| 438 | Pre Clean Cycle Indicator - Finish | Panel Mounted LED |
| 440 | Pre Clean Cycle Indicator - Low Level | Panel Mounted LED |
| 442 | Pre Clean Cycle Indicator - Vacuum | Panel Mounted LED |
| 444 | Sterilization Cycle Indicator - Auto | Panel Mounted LED |
| 446 | Sterilization Cycle Indicator - Manual | Panel Mounted LED |
| 448 | Volt Meter (digital) | Mfg. Simpson DC Voltage Indicators 12/24/48 VDC Model M245 |
| 450 | Ammeter (digital) | Mfg. Simpson DC Current Indicators 12/24/48 VDC Model M245 |
| 452 | Electrolyzation Control (on/off & variable) Switch | Mfg. Lutron Dimmer Switch Skylark S-600P 120AC 50 Hz SA (including a two-position on/off control and a sliding variable control) |
| 454 | Pre Clean Pump (on/off & variable) Switch | Same |
| 456 | Post Clean Pump (on/off & variable) Switch | Same |
| 458 | Sterilization Cycle Switch (Auto/Manual) Switch | Panel Mounted Switch |
| 460 | Auto - Pre Clean/Post Clean Vacuum Switch | Panel Mounted Switch |
| 462 | Manual - Pre Clean Switch | Panel Mounted Switch |
| 464 | Manual - Post Clean Switch | Panel Mounted Switch |
| 466 | Manual - Vacuum Switch | Panel Mounted Switch |
| 468 | Pre Clean Drain Switch | Panel Mounted Switch |
| 470 | Post Clean Drain Switch | Panel Mounted Switch |

Figure 10C:
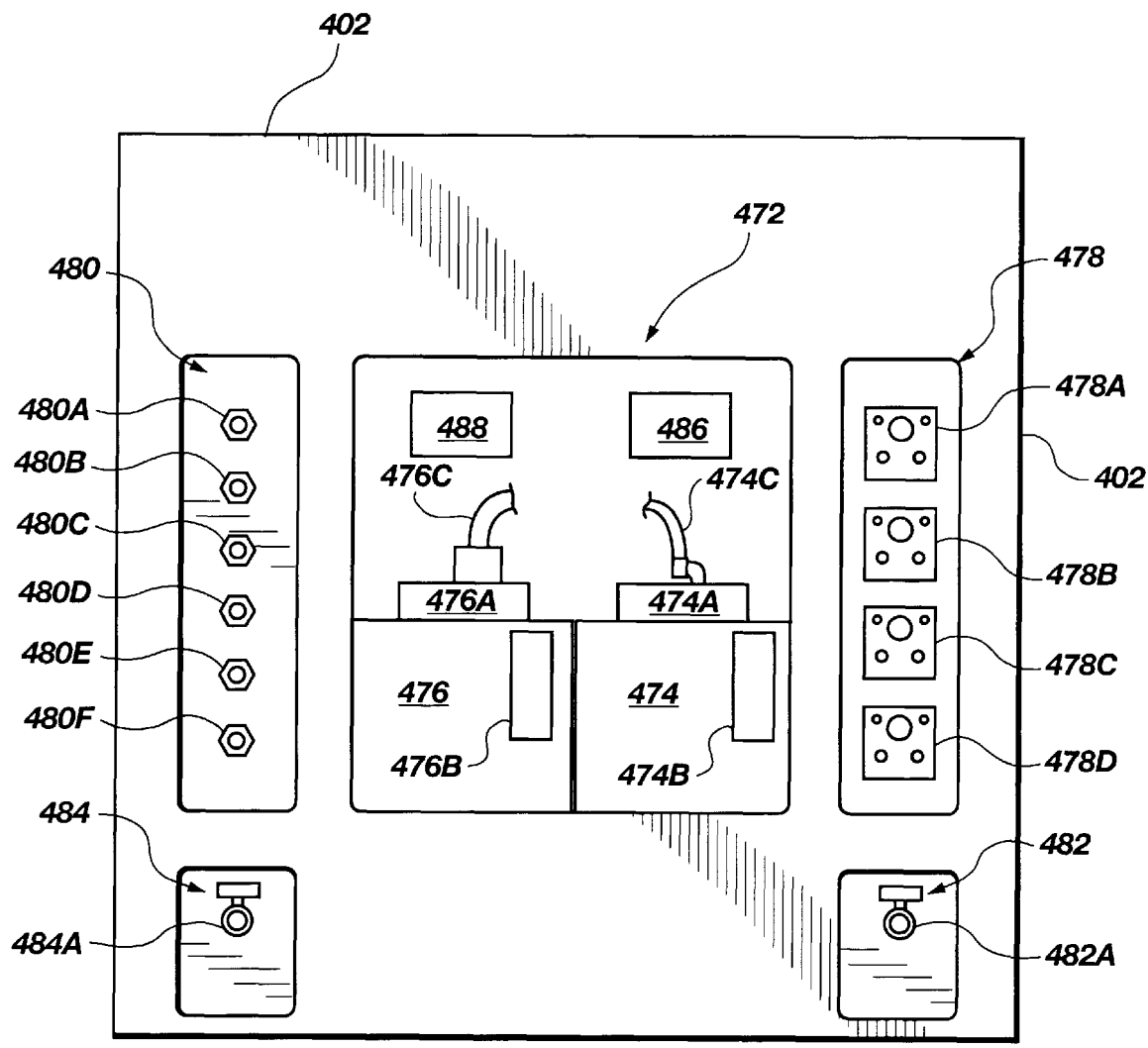
FIG. 10C is a front view of the fourth embodiment represented in FIG. 10A.

Reference will next be made to FIG. 10C which is a front view of the automatic sterilizer 400 represented in FIG. 10A. Represented in FIG. 10C is an internal compartment, generally indicated at 472, contained within the housing 402 and holding selected components. Also represented is a timer compartment, generally indicated at 478, a circuit breaker/switch compartment, generally indicated at 480, an electrolyzed saline sampling compartment, generally indicated at 482, and a sterile water sampling compartment, generally indicated at 484. It is preferred that each of the compartments (generally indicated at 472, 478, 480, 482, and 484) are provided with hinged doors which are not represented in the figures to improve the clarity thereof.

Located in the internal compartment 472 is an electrolyzed saline container 474 which includes a lid 474A, a viewing window 474B, and a communication tube 474C which leads to the other components of the automatic sterilizer 400. While it is preferred that appropriate saline solution be placed into the electrolyzed saline solution and then the saline solution subjected to electrolysis, it is also within the scope of the present invention to install previously electrolyzed saline solution into the electrolyzed saline container 474.

Also located in the internal compartment 472 is a sterile water container 476 which includes a lid 476A, a viewing window 476B, and a communication tube 476C which leads to the other components of the automatic sterilizer 400. The sterile water container 476 holds a fluid which is used to flush and rinse the items being sterilized and, if necessary, to replenish water used in the saline solution.

Represented in FIG. 10C are a number of controls and indicators which interface with other components of the automatic sterilizer 400, all of which can be readily selected and constructed by one skilled in the art using the information provided herein. Provided in Table D is a description of, as well as an explanation of the function of, the controls and indicators grouped in FIG. 10C, in the timer compartment 478, the circuit breaker/switch compartment 480, the saline sampling compartment 482, and the sterile water sampling compartment 484.

TABLE D

| Control/Indicator | Function | Exemplary Preferred Components |
|---|---|---|
| 478A | Automatic Timer | AGASTAT ® Timer 48K90US Multi-mode, Multi-range Timer 0.1 sec to 10 hrs Input Power:24–125 VDC 24–240 VAC, 50/60 Hz Output Contact Rating: |

TABLE D-continued

| Control/Indicator | Function | Exemplary Preferred Components |
|---|---|---|
| | | 10A @ 120/240 VAC or 30 VDC resistive Same polarity |
| 478B | Pre Clean Timer | Same |
| 478C | Post Clean Timer | Same |
| 478D | Pre Clean Timer | Same |
| 480A | Main Circuit Breaker | Panel Mounted Circuit Breaker |
| 480B | Pre Clean Circuit Breaker | Panel Mounted Circuit Breaker |
| 480C | Post Clean Circuit Breaker | Panel Mounted Circuit Breaker |
| 480D | Electrolyzer Circuit Breaker | Panel Mounted Circuit Breaker |
| 480E | Pump Switch | Panel Mounted Switch |
| 480F | Main Power Switch | Panel Mounted Key Switch |
| 482A | Electrolyzed Saline Sampling Outlet | Plastic Valve |
| 484A | Sterile Water Sampling Outlet | Plastic Valve |

A pump device 486 is represented in FIG. 10C and those skilled in the art can readily select an appropriate pump device from those available in the art. One preferred pump is available under the trademark FLOJET (model 2100--034--115, Voltage 115 Volts AC [50/60 Hz], 0.50 Amps, Flow 0.8 G.P.M. [3.0LPM]max, Pressure 60 PSI [4.1 BAR] max) but other pumps can also be used in accordance with the present invention. A vacuum source 488 is also preferably included and a vacuum source can be included in the automatic sterilizer 400 or an external vacuum source, as available in health care facilities, can be used.

Figure 10D:
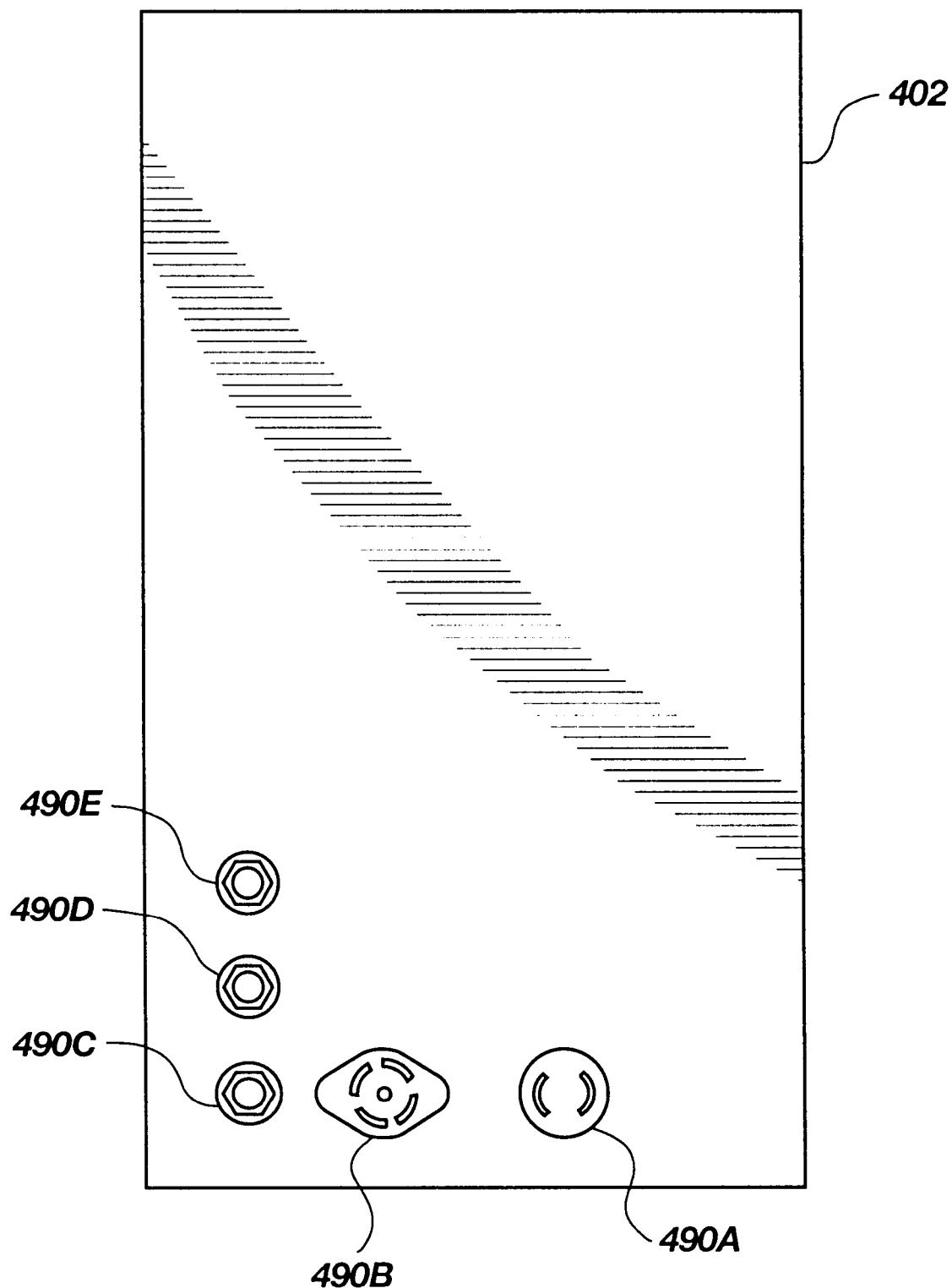
FIG. 10D is a side view of the fourth embodiment represented in FIG. 10A.

Represented in FIG. 10D are a number of connectors which convey power and fluids to other components of the automatic sterilizer 400, all of which can be readily selected and constructed by one skilled in the art using the information provided herein. Provided in Table E is a description of the connectors illustrated in FIG. 10D and their function.

TABLE E

| Connector | Function |
|---|---|
| 490A | Vacuum Pump AC Outlet |
| 490B | 110 VAC Inlet |
| 490C | Post Clean Drain Port |
| 490D | Pre Clean Drain Port |
| 490E | Vacuum Inlet/Outlet |

It will be appreciated that additional embodiments of the present invention can be arrived out utilizing fewer components than described herein with the understanding the automatic sterilizer 400 described herein is configured for greatest flexibility and utility with a variety of different items to be sterilized and determining the efficiency of the sterilization which is carried out.

It is preferred that the automatic sterilizer 400 be used by first removing the lid 476A, filling the sterile water container 476 with three liters of sterile water, and replacing the lid 476A. A saline solution is then prepared by mixing about thirty grams of sodium chloride in three liters of water and the saline solution is placed in the container 474. One preferred concentration of sodium chloride is 1.0% but other concentrations can also be used within the scope of the present invention. Power is applied to the automatic sterilizer 400 by turning on main power switch 480F which causes cooling fans to come on and appropriate indicators to light. The sterilization cycle switch (auto/manual) 458 is set to the manual position and the pre clean pump (on/off & variable) switch 454 is set to the on position. The electrolyzation control (on/off & variable) 454 is adjusted to obtain the desired voltage and current. One liter of electrolyzed saline solution is preferably withdrawn through the electrolyzed saline sampling outlet 482A, a surfactant is added, mixed, and returned to the electrolyzed saline solution container 474.

The addition of a surfactant increases the efficiency of the sterilization process and particularly improves the sterilization of the turbine components within the dental drill handpiece D. Many different surfactants can be used in accordance with the present invention. Two preferred surfactants are those known in the industry as Varox 365 (Witco Corp. of Dublin, Ohio) and Dowfax (The Dow Chemical Co. of Midland, Mich.). The preferred concentration for the surfactant is 0.01% but other concentrations can also be used in accordance with the present invention.

After the sufactant is added to the automatic sterilizer 400, pre clean pump (variable) switch 454 is adjusted until the flow meter 418 reads the desired value, preferably about 200 ml per minute, for about fifteen minutes and then the pre clean pump switch 454 (on/off) is turned off. The dental drill handpiece D is then attached via the coupler 412. It is preferred that a blank burr be inserted into the dental drill handpiece D, but sterilization can be carried out without inserting such a blank.

After the dental drill handpiece D is attached to the coupler 412, the automatic sterilizer 400 can be advantageously operated in a manual fashion or in an automatic fashion. To carry out manual operation, the pre clean pump switch (on/off) 454 is moved to the on position and then the pre clean pump switch (variable) is adjusted until the flow meter 418 reads the desired value. After sterilization has occurred for the desired time period, the pre clean pump switch (on/off) 454 is moved to the off position. The manual vacuum switch 466 is then turned on which causes a vacuum to remove fluid from the dental drill handpiece D and the sterilizing chamber 406. The post cleaner pump switch (on/off) 456 and the post cleaner pump switch (variable) 456 are activated to rinse the dental drill handpiece D and the sterilizing chamber 406 with sterile water. After the rinse is complete, the manual vacuum switch 466 is activated to remove fluid from the dental drill handpiece D and the sterilizing chamber 406.

To carry out automatic operation, the sterilization cycle switch (auto/manual) switch 458 is moved to the automatic position and the auto—pre clean/post clean vacuum switch 460 is activated. Sterilization, rinsing, and removal of the fluid, continues for the predetermined period of time, which when completed, the dental drill handpiece D is removed.

After carrying out sterilization for a period of time, the fluids should be replaced. To remove the fluids, the pre clean drain switch 468 is moved to its on position and the pre clean pump (on/off & variable) 454 is activated to drain the electrolyzed saline solution through the post clean drain port 490C. The activation of the post clean drain switch 470 similarly causes the draining of the sterile water from the automatic sterilizer 400. Advantageously, the fluids which are drained from the automatic sterilizer 400 can generally be discharged into the environment without any concern regarding toxicity or harm. Moreover, the automatic sterilizer 400 can readily provide sterilization of dental drill handpieces D in a convenient period of time, i.e. in minute, particularly when compared to previously available sterilization methods and devices.

Figure 11A:
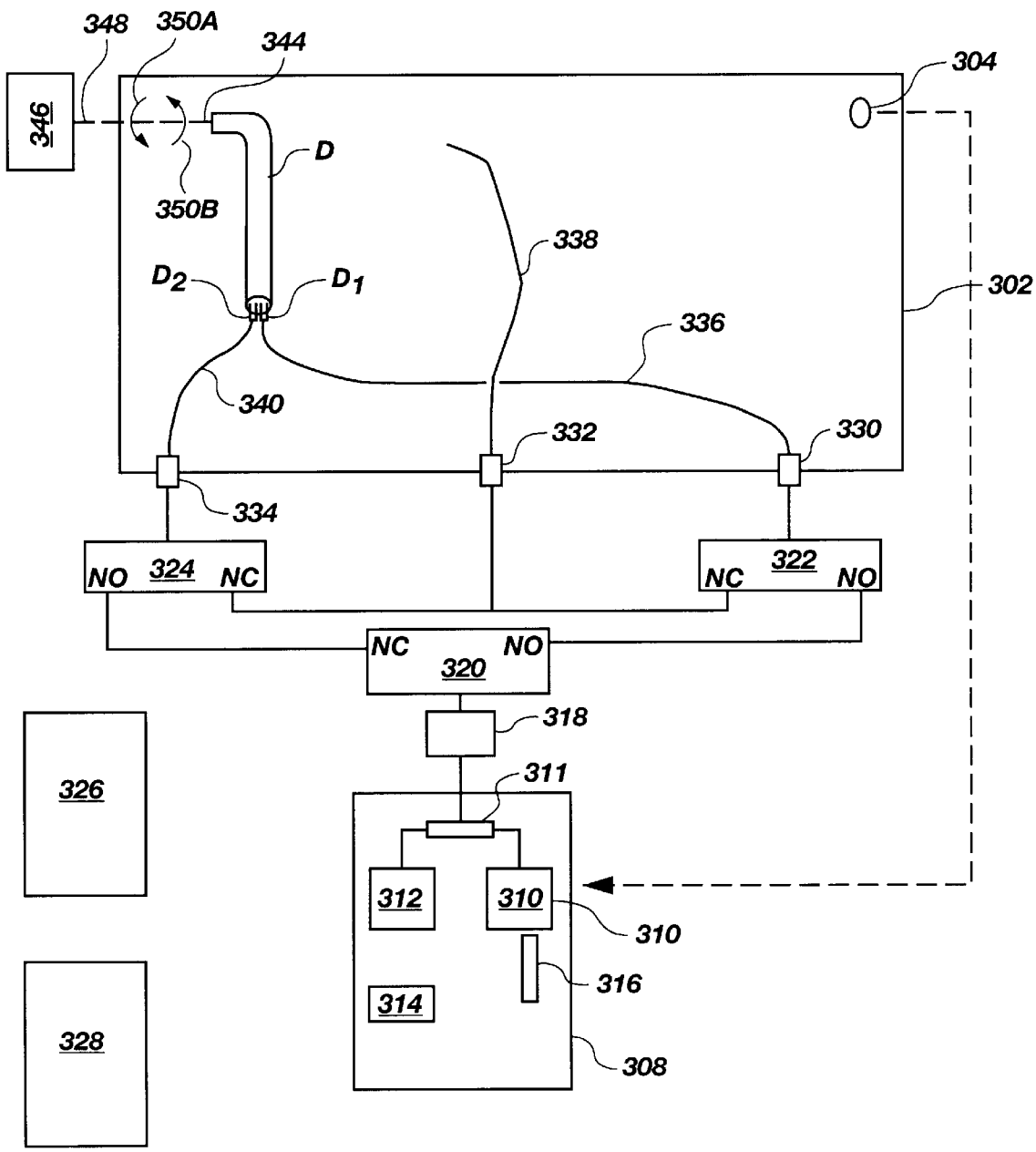
FIG. 11A is a block diagram representing a fifth presently preferred embodiment of the present invention particularly adapted for automatically sterilizing dental equipment.
Figure 11B:
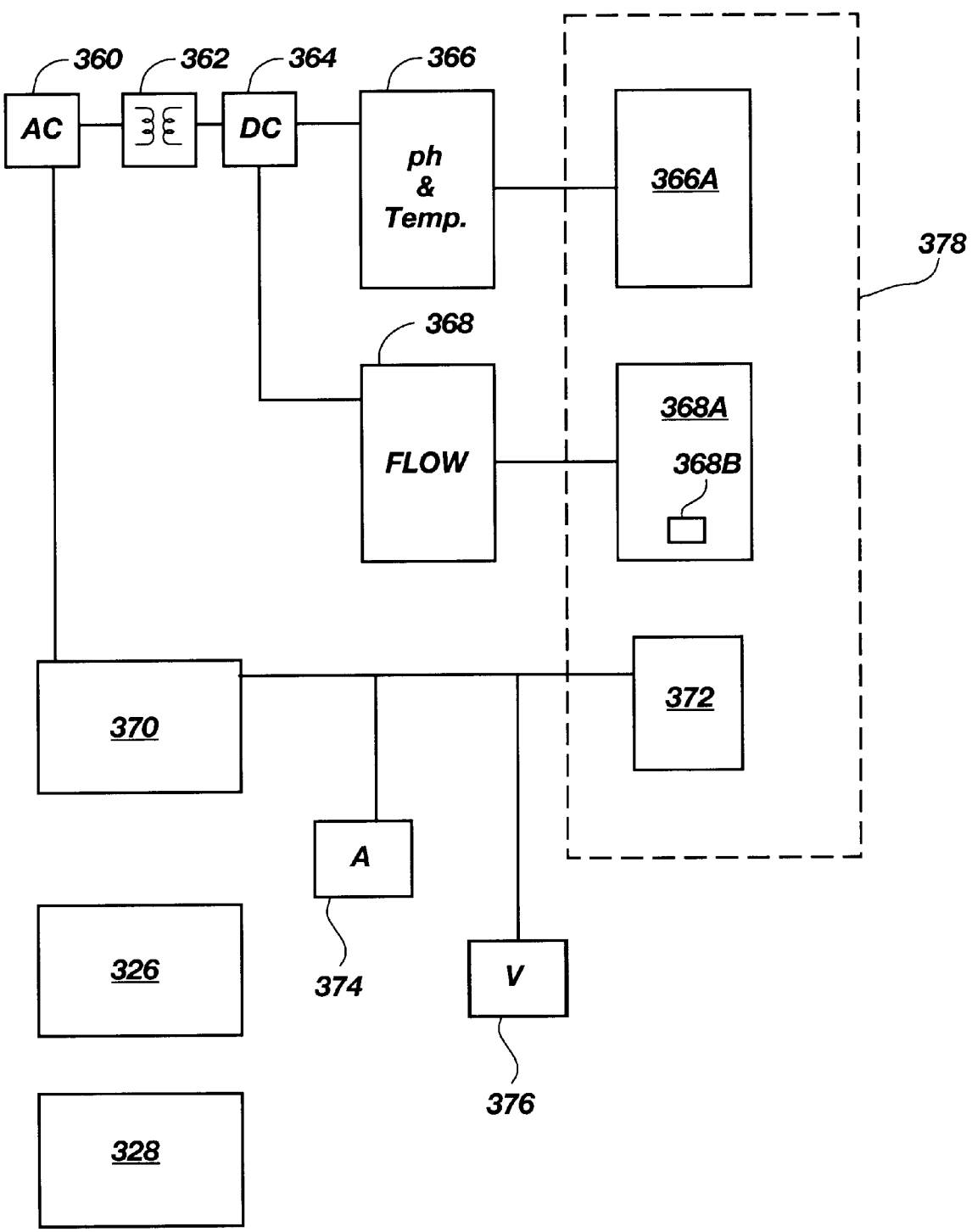
FIG. 11B is a block diagram representing the electrical components of the fifth embodiment represented in FIG. 11A.

Reference will next be made to FIG. 11A which is a block diagram representing a fifth presently preferred embodiment of the present invention particularly adapted for automatically sterilizing dental equipment. The diagram of FIG. 11A represents the principal fluidic and mechanical components of the preferred fifth embodiment of the present invention. FIG. 11B will be referred to shortly to describe the principal electrical components of the preferred fifth embodiment of the present invention.

Represented in FIG. 11A is a fluid processing compartment 308 which includes an electrolyzed saline container 310 and a sterile water container 312. The components necessary to electrolyze the saline solution are represented at 316. A diverter valve 311 determines whether electrolyzed saline solution (container 310) or sterile water (container 312) will be passed to a pump 318 and onto other components of the apparatus. The diverter valve 311 is preferably an electrically operated diverter valve, as are all of the diverter valves described in connection with FIG. 11A, and their operation is coordinated via a controller 326. One diverter valve preferred for use with the present invention is manufactured by Burkert, 120 V 60 HZ 8 W, Model W3YUE. It is also within the scope of the present invention to include a microprocessor based control unit, such as a PC compatible computer 328, to manage and record the functions of the apparatus represented in FIGS. 11A&B. Those skilled in the art can readily arrive at appropriate interfaces between the computer 328 or the timer 326 and the other components represented in FIGS. 11A&B. For example, it is within the scope of the present invention to provide embodiments of the present invention in which the operation of the sterilization operation is monitored and the operation of the embodiment is altered in real time to provide optimum results. Those skilled in the art will readily be able to arrive at the necessary interface components to provide efficient operation of the apparatus. Moreover, those skilled in the art will appreciate that many different structures can be used to move fluid through the apparatus other than the pump 318.

Represented in FIG. 11A is a surfactant storage container 314. The preferred sufactant can be those discussed previously. The surfactant held in surfactant storage container 314 is metered into the electrolyzed saline solution container 310 or the sterile water container 312, as desired to increase the efficiency of the sterilization procedure. Most preferably the surfactant is only metered into the electrolyzed saline solution container 310 so that the sterile water can be used to completely rinse any electrolyzed saline solution from the dental drill handpiece D.

The diverter valves 320, 322, and 324 are operated so that sterilizing fluid is first directed through the dental drill handpiece D in a first direction and then, after a period of time, in the reverse direction. One of the most difficult portions of a dental drill handpiece D to sterilize, i.e. inactivate all spores of particularly hardy test microorganisms, is the turbine blades contained within the dental drill handpiece. The dental drill handpiece D includes an air drive conduit $D_1$ and an air exhaust conduit $D_2$ to which the fluid lines 336 and 340 are attached via a coupler diagrammatically represented at 412. The fluid lines 336 and 340 are in communication with diverter valves 322 and 324, respectively, via connectors 330 and 334, respectively. The dental drill handpiece D is held in a tray 302 and is bathed in the sterilizing fluid which exits fluid line 338 which is attached to connector 332. The sterilizing fluid drains from the tray 302 via a drain 304 and is recirculated in accordance with the previously described procedures.

As known in the industry, the dental drill handpiece D also includes conduits which are used to convey water and air to the head of the dental drill handpiece. It is within the scope of the present invention to pass sterilizing fluid through the conduits which convey water and air, both unidirectionally and bidirectionally. The coupler 412 (FIG. 10B) can be used to provide convenient simultaneous coupling to the conduits which convey water and air to the head of the dental drill handpiece D, in addition to coupling to the conduits which convey air to and from the turbine.

It is also preferred that structures are included to control the rotation of the turbine within the dental drill handpiece D. It has been found that controlling the rotation of the turbine to a value which is different than that which would be obtained if the turbine is allowed to rotate at the speed caused by the flow of the sterilizing fluid through the turbine provides great benefits. Represented in FIG. 11A is an engagement member 344, which can preferably be fashioned as a blank burr, which is connected to a motor 346. The motor 346 can preferably be one available from Synchron, part no. 30-93-B. The motor 346 is coupled to the engagement means 344 via an interconnecting shaft 348. The illustrated arrangement preferably provides rotation of the turbine in the direction of arrows 350A and 350B. The motor 346 is controlled to provide rotation of the turbine in the range from about one rotation each second to about one rotation each five minute internal with a value of one rotation (carried out in steps) each thirty second interval being somewhat preferred but many different values can also be used within the scope of the present invention. Moreover, the rotation can occur in just one direction (350A or 350B) or can occur first one direction and then in the opposite direction. Furthermore, the rotation can be alternated with intermittently holding the turbine still. Controlling the rotation of the turbine provides the unexpected result of improved sterilization when sterilizing fluid is passed through the turbine. It will be appreciated that many different approaches to controlling the rotation of the turbine provides greatly improved sterilization.

Reference will next be made to FIG. 11B which is a block diagram representing the electrical components also preferably associated with the fifth presently preferred embodiment of the present invention described in connection with FIG. 11A. Represented in FIG. 11B is an AC power source, a transformer 362, and a DC power source 364. It will be appreciated that the embodiments of the present invention described herein can be powered from an internal or external battery or some other power source to allow operation away from an AC power source. For example, all of the embodiments of the present invention described herein can greatly benefit a veterinary practice and providing battery power allows portable operation in the field.

Still referring to FIG. 11B, a pH and temperature detection device 366 and a flow rate detection device 368 are also provided. A pH and temperature probe 366A is placed in the fluid path (designed by the box 378) and connected to the pH and temperature detection device 366. Similarly, a flow indicator probe 368A, which includes a filter 368B, is also place in the fluid path 378 and connected to the flow rate detection device 368. A hydrolyzation unit 370 includes the electrical components which are necessary to operate the electrode 372 placed in the fluid path to electrolyze saline solution. A current detection device 374 and a voltage detection device 376 are also preferably included to monitor the voltage and current applied to the electrode 372. It will be appreciated that if a sterilizing solution other electrolyzed saline solution is used, one or more of the components represented in FIG. 11B may be omitted in accordance with the present invention.

Using the apparatus represented in FIGS. 10A–D and in FIGS. 11A–B, sterilization of items can be carried out much faster, and in the case of delicate items, much more gently, than previously possible. For example, the present invention can be used to sterilize items fabricated from plastic which otherwise would be difficult to effectively sterilize. The present invention is particularly useful for sterilizing tubing and lines which are used carry fluids which may come into contact with humans, for example, lines which carry air and water to a dental drill handpiece. Most advantageously, using the described embodiments, complete sterilization of a dental drill handpiece can be carried out in not more than about ten minutes, more preferably in not more than about five minutes, and most preferably in not more than about three minutes.

Moreover, those skilled in the art will be able to arrive at many additional embodiments of the invention by combining the features and structures described herein to provide an apparatus which is particularly adapted for one of the end uses set forth herein.

From the foregoing, it will be appreciated that the present invention provides an efficient system and procedure to prevent the transfer of harmful microbes via health care equipment from one patient to another patient and for sterilizing health care instruments. The present invention also provides a system and method for sterilizing medical and dental instruments which is effective and not damaging to the instruments and which can kill infectious spores present on medical and dental instruments to prevent infection of a subsequent patient without damaging the instrument. The present invention also provides efficient apparatus and methods for disinfecting and sterilizing many items which benefit from such treatments.

The present invention also provides an apparatus and method for electrolyzing saline solutions which are particularly suitable for administration in vivo and which does not introduce harmful substances into the electrolyzed fluid. The present invention also provides an apparatus and method for electrolyzing saline solutions which is reliable and can be economically operated.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A system for sterilizing equipment which includes at least one conduit through the equipment, the system comprising:
   a) means for electrolyzing a saline solution to produce an electrolyzed saline solution comprising:
      i) a first electrode comprised of a first anode having a cylindrical shape;
      ii) a second electrode comprised of a first cathode having a substantially cylindrical shape and positioned concentrically in relation to the anode; and
      iii) power supply means for providing a source of electrical current, the power supply means conveying electrical current to the first electrode and the second electrode;
   b) means for holding the electrolyzed saline solution;
   c) means for holding the equipment;
   d) means for directing the electrolyzed saline solution into the conduit; and
   e) means for directing the electrolyzed saline solution to the means for holding the electrolyzed saline solution after passing through the conduit such that any microbes present in the conduit are killed.

2. A system for sterilizing equipment as defined in claim 1 further comprising means for flowing the electrolyzed saline solution over the surface of the equipment such that any microbes present on the surface of the equipment are killed.

3. A system for sterilizing equipment as defined in claim 1 wherein the first electrode comprises a cylindrical shape having first side and a second side and a passageway extending from the first side to the second side.

4. A system for sterilizing equipment as defined in claim 1 wherein the means for holding the electrolyzed saline solution comprises a holding tray.

5. A system for sterilizing equipment as defined in claim 1 wherein the means for holding the equipment comprises means for holding dental drill handpieces.

6. A system for sterilizing equipment as defined in claim 1 wherein the means for holding the equipment comprises a length flexible tubing.

7. A system for sterilizing equipment as defined in claim 1 wherein the means for the flowing the electrolyzed saline solution over the equipment comprises a pump.

8. A system for sterilizing equipment as defined in claim 1 wherein the means for the flowing the electrolyzed saline solution over the equipment comprises means for recirculating the electrolyzed saline solution from the means for electrolyzing saline solution to the means for holding the equipment.

9. A system for sterilizing equipment as defined in claim 1 comprising a temperature detection device facilitating maintaining the electrolyzed saline solution at a temperature of less than 100 degrees Celsius.

10. A system for sterilizing equipment as defined in claim 1 wherein the equipment comprises dental equipment.

11. A system for sterilizing equipment as defined in claim 1 wherein the equipment comprises medical equipment.

12. A system for sterilizing equipment as defined in claim 1 wherein the equipment comprises veterinary equipment.

13. A system for sterilizing equipment as defined in claim 12 wherein the means for electrolyzing saline comprises a battery.

14. A system for sterilizing dental drills which include a turbine and a rotatable shaft connected to the turbine, and a conduit connected to the turbine, the sterilization occurring at a temperature substantially less than 100 degrees Celsius, the system comprising:
   means for holding the electrolyzed saline solution;
   means for holding the dental drill;
   means for directing the electrolyzed saline solution into the conduit; and
   means for controlling the rotation of the turbine as electrolyzed saline solution passes through the conduit and through the turbine such that any microbes present in the conduit and in the turbine are substantially killed.

15. A system for sterilizing dental drills as defined in claim 14 further comprising means for flowing the electrolyzed saline solution over the surface of the dental drill as electrolyzed saline solution passes through the conduit such that any microbes present on the surface of the equipment are killed.

16. A system for sterilizing dental drills as defined in claim 14 wherein the means for controlling the rotation of the turbine comprises means for making mechanical connection with the shaft of the turbine and rotating said shaft in steps, each step being less than 360°.

17. A system for sterilizing dental drills as defined in claim 16 further comprising means for flowing the electrolyzed saline solution over the surface of the dental drill as electrolyzed saline solution passes through the conduit such that any microbes present on the surface of the equipment are killed.

18. A system for sterilizing dental drills as defined in claim 14 wherein the means for controlling the rotation of the turbine comprises rotating the turbine once every three times.

19. A system for sterilizing dental drills as defined in claim 14 wherein the means for further comprising means for flowing the electrolyzed saline solution over the surface of the dental drill as electrolyzed saline solution passes through the conduit such that any microbes present on the surface of the equipment are killed.

20. A system for sterilizing dental drills as defined in claim 14 wherein the means for electrolyzing saline solution comprises:

first electrode means;

second electrode means; and power supply means for providing a source of electrical current, the power supply means conveying electrical current to the first electrode and the second electrode.

21. A system for sterilizing dental drills as defined in claim 20 wherein the first electrode comprises:

a first anode comprising a cylindrical shape; and
wherein the second electrode comprises:

a first cathode comprising a substantially cylindrical shape and positioned concentrically in relation to the anode.

22. A system for sterilizing dental drills as defined in claim 20 wherein the first electrode comprises a cylindrical shape having first side and a second side and a passageway extending from the first side to the second side.

23. A system for sterilizing dental drills as defined in claim 14 wherein the means for holding the electrolyzed saline solution comprises a tray.

24. A system for sterilizing dental drills as defined in claim 14 wherein the means for holding the equipment comprises a length flexible tubing and a means for connecting to the conduit.

25. A system for sterilizing equipment as defined in claim 14 comprising a temperature detection device facilitating maintaining the electrolyzed saline solution at a temperature of less than 100 degrees Celsius.

26. A system for sterilizing dental drills which include a turbine and a rotatable shaft connected to the turbine, and a conduit connected to the turbine, the system comprising:

means for holding a sterilizing solution;

means for holding the dental drill;

means for directing the sterilizing solution into the conduit; and means for controlling the rotation of the turbine as sterilizing solution passes through the conduit and through the turbine such that any microbes present in the conduit and in the turbine are substantially killed.

27. A system for sterilizing equipment which includes at least one conduit through the equipment, the system comprising:

a) means for electrolyzing a saline solution to produce an electrolyzed saline solution comprising:

i) a first electrode comprising a cylindrical shape having a first side and a second side and a passageway extending from the first side to the second side;

ii) a second electrode; and iii) a power supply for providing a source of electrical current, the power supply means conveying electrical current to the first electrode and the second electrode;

b) means for holding the electrolyzed saline solution;

c) means for holding the equipment;

means for directing the electrolyzed saline solution into the conduit; and d) means for directing the electrolyzed saline solution to the means for holding the electrolyzed saline solution after passing through the conduit such that any microbes present in the conduit are killed.

28. A system for sterilizing equipment which includes at least one conduit through the equipment, the system comprising:

means for electrolyzing a saline solution to produce an electrolyzed saline solution;

means for holding the electrolyzed saline solution;

means for holding dental drill handpieces;

means for directing the electrolyzed saline solution into the conduit; and means for directing the electrolyzed saline solution to the means for holding the electrolyzed saline solution after passing through the conduit such that any microbes present in the conduit are killed.

29. A system for sterilizing equipment which includes at least one conduit through the equipment, the system comprising:

means for electrolyzing a saline solution to produce an electrolyzed saline solution;

means for holding the electrolyzed saline solution;

means for holding the equipment comprised of a length flexible tubing;

means for directing the electrolyzed saline solution into the conduit; and means for directing the electrolyzed saline solution to the means for holding the electrolyzed saline solution after passing through the conduit such that any microbes present in the conduit are killed.

30. A system for sterilizing equipment which includes at least one conduit through the equipment, the system comprising:

means for electrolyzing a saline solution to produce an electrolyzed saline solution comprised of a battery;

means for holding the electrolyzed saline solution;

means for holding the equipment;

means for directing the electrolyzed saline solution into the conduit; and means for directing the electrolyzed saline solution to the means for holding the electrolyzed saline solution after passing through the conduit such that any microbes present in the conduit are killed.

* * * * *